(12) United States Patent
Mauro et al.

(10) Patent No.: US 8,853,179 B2
(45) Date of Patent: Oct. 7, 2014

(54) REENGINEERING MRNA PRIMARY STRUCTURE FOR ENHANCED PROTEIN PRODUCTION

(75) Inventors: Vincent P. Mauro, San Diego, CA (US); Stephen A. Chappell, San Diego, CA (US); Wei Zhou, San Diego, CA (US); Gerald M. Edelman, San Diego, CA (US)

(73) Assignee: The Scripps Research Institute, LaJolla, CA (US)

( * ) Notice: Subject to any disclaimer, the term of this patent is extended or adjusted under 35 U.S.C. 154(b) by 93 days.

(21) Appl. No.: 13/203,229

(22) PCT Filed: Feb. 24, 2010

(86) PCT No.: PCT/US2010/000567
§ 371 (c)(1),
(2), (4) Date: Nov. 3, 2011

(87) PCT Pub. No.: WO2010/098861
PCT Pub. Date: Sep. 2, 2010

(65) Prior Publication Data
US 2012/0053333 A1    Mar. 1, 2012

Related U.S. Application Data

(60) Provisional application No. 61/155,049, filed on Feb. 24, 2009.

(51) Int. Cl.
*C12N 15/11*    (2006.01)
*C12P 21/02*    (2006.01)

(52) U.S. Cl.
CPC ............. *C12P 21/02* (2013.01); *C12N 2320/53* (2013.01); *C12N 2320/50* (2013.01); *C12N 15/111* (2013.01); *C12N 2310/141* (2013.01)
USPC ...................................................... 514/44 A

(58) Field of Classification Search
USPC ...................................................... 514/44 A
See application file for complete search history.

(56) References Cited

U.S. PATENT DOCUMENTS

| | | | |
|---|---|---|---|
| 5,914,269 A | 6/1999 | Bennett et al. | |
| 2003/0158133 A1 | 8/2003 | Movsesian | |
| 2006/0265771 A1 | 11/2006 | Lewis et al. | |

OTHER PUBLICATIONS

Kwon et al. Archives of Biochemistry and Biophysics vol. 386, 163-171, 2001.*
Kozak. "Adherence to the First-AUG Rule When a Second AUG Codon Follows Closely Upon the First." *Proceedings of The National Academy of Sciences.* vol. 92. No. 7. (Mar. 28, 1995): pp. 2662-2666.
Kozak. "Pushing the limits of the scanning mechanism for initiation of translation." *Gene.* Elsevier, Amsterdam, NL. vol. 299. No. 1-2. (Oct. 16, 2002): pp. 1-34.
Kozak. "Regulation of translation via mRNA structure in prokaryotes and eukaryotes." *Gene.* Elsevier, Amsterdam, NL. vol. 361. (Nov. 21, 2005): pp. 13-37.
Liu et al. "Efficient and Isoform-Selective Inhibition of Cellular Gene Expression by Peptide Nucleic Acids+." *Biochemistry.* vol. 43. No. 7. (Feb. 1, 2004): pp. 1921-1927.
Preiss et al. "Dual function of the messenger RNA cap structure in poly (A)—tail—promoted translation in yeast." *Nature: International Weekly Journal of Science*, Nature Publishing Group,United Kingdom. vol. 392. No. 6675. (Apr. 2, 1998): pp. 516-520.
Vivier et al. "Functional analysis of multiple AUG codons in the transcripts of the STA2 glucoamylase gene from *Saccharomyces cerevisiae.*" *Mon Gen Genet*.vol. 261. (Jan. 1, 1999): pp. 11-20.
Xiong et al. "Regulation of CCAAT/enhancer-binding protein-beta isoform synthesis by alternative translational initiaiton at multiple AUG start sites." *Nucleic Acids Research.* vol. 29, No. 14. (Jul. 15, 2001): pp. 3087-3098.
PCT International Search Report and Written Opinion dated Apr. 21, 2010, issued in connection with counterpart PCT Application No. PCT/US2010/000567.
Chappell et al. "Ribosomal shunting mediated by a translational enhancer element that base pairs to 18S rRNA" *PNAS* 103(25):9488-9493 (2006).
Eulalio et al."Getting to the root of miRNA-mediated gene silencing" *Cell* 132:9-14 (2008).
Genbank Database [online], Feb. 6, 2002, Jiang et al.: '*Caenorhabditis elegans* hypoxia-induced factor 1 mRNA, complete cds', [retrieved on Jul. 7, 2012], Accession No. AF364604.
Genbank Database [online], Jul. 8, 2012, Sousa et al.: *Homo sapiens* interleukin 6 (interferon, beta 2) (IL6), mRNA. [retrieved on Jul. 12, 2012] Accession No. NM_000600.
Genbank Database [online], Jul. 8, 2012, Su et al.: '*Homo sapiens* erythropoietin (EPO), mRNA.' [retrieved on Jul. 12, 2012], Accession No. NM_000799.
Genbank Database [online], Nov. 8, 1994, Van Straaten, et al.: 'Human fos proto-oncogene (c-fos), complete cds.' [retrieved on Jul. 7, 2012], Accession No. K00650.
Genbank Database [online], Jul. 10, 1992, Lyle et al.: 'transcription factor NF-kappa B.' [retrieved on Jul. 7, 2012], Accession No. 2006293A.
Genbank Database [online], Apr. 17, 2009, Dobbins et al.: 'DNA-directed RNA polymerase [Enterbacteria phage SP6].' [retrieved on Jul. 9, 2012], Accession No. NP_853568.
Genbank Database [online], Apr. 17, 2009, Pajunen et al.: 'RNA polymerase [Enterobacteria phage T3].' [retrieved on Jul. 7, 2012], Accession No. NP_523301.
Genbank Database [online], Dec. 19, 2002. Yao et al.: 'Synthetic construct Gal4 DNA-binding domain/VP16 activation domain fusion protein mRNA, complete cds.', [retrieved on Jul. 7, 2012], Accession No. AY136632.

(Continued)

*Primary Examiner* — Brian Whiteman
(74) *Attorney, Agent, or Firm* — Ivor Elrifi; Christina K. Stock; Cooley LLP

(57) ABSTRACT

Described herein are rules to modify natural mRNAs or to engineer synthetic mRNAs to increase their translation efficiencies. These rules describe modifications to mRNA coding and 3' UTR sequences intended to enhance protein synthesis by: 1) decreasing ribosomal diversion via AUG or non-canonical initiation codons in coding sequences, and/or 2) by evading miRNA-mediated down-regulation by eliminating one or more miRNA binding sites in coding sequences.

1 Claim, 5 Drawing Sheets

(56) References Cited

OTHER PUBLICATIONS

Genbank Database [online], Dec. 22, 1993, Nakamura et al.: 'H.sapiens mRNA for tre oncogene (clone 213).' [retrieved on Jul. 7, 2012], Accession No. X63547.
Genbank Database [online], Apr. 24, 1993, Reddy et al.: 'Human DNA for c-ets-1 proto-oncogene.' [retrieved on Jul. 7, 2012], Accession No. X14798.
Genbank Database [online], Feb. 24, 2004, Strausberg et al.: 'Homo sapiens zinc finger protein 576, mRNA (cDNA clone MGC: 2508, Image: 35359910, complete cds.' [retrieved on Jul. 7, 2012], Accession No. BC002981.
Genbank Database [online], Oct. 26, 1993, Ikeda et al.: 'RNA polymerase, partial [Enterobacteria phage T7]', [retrieved on Jul. 7, 2012], Accession No. AAB28111.
Genbank Database [online], Apr. 27, 1993, Dorfman et al.: 'Human transcription factor GATA-2 (GATA-2) mRNA, complete cds.' [retrieved on Jul. 7, 2012], Accession No. M77810.
Genbank Database [online], Apr. 27, 1993, Hoeffler et al.: 'Human transactivator protein (CREB) mRNA, complete cds.' [retrieved on Jul. 7, 2012], Accession No. M27691.
Genbank Database [online], Apr. 27, 1993, Laughon et al.: 'Yeast (S. cerevisiae) GAL4 gene coding for a positive regulator of galactose inducible genes.' [retrieved on Jul. 7, 2012], Accession No. K01486.
Genbank Database [online], Apr. 27, 1993, Pinney et al.: 'M.musculus MyoD mRNA, complete cds.' [retrieved on Jul. 7, 2012], Accession No. M84918.
Genbank Database [online], Apr. 27, 1993, Rabbitts et al.: 'Human (Daudi) translocated t(8; 14) c-myc oncogene mRNA, complete cds.' [retrieved on Jul. 7, 2012], Accession No. K02276.
Genbank Database [online], May 31, 1994, Jacobs et al.: 'Human MYB DNA binding protein (c-myb) gene, 5' end.' [retrieved on Jul. 7, 2012], Accession No. M95584.
Henikoff & Henikoff, "Amino Acid substitution matrices from protein blocks", *Proc. Natl. Acad. Sci. USA* 89:10915 (1989).
Hu et al. "rRNA-complementarity in the 5' untranslated region of mRNA specifying the Gtx homeodomain protein: Evidence that base-pairing to 18S rRNA affects translational efficiency" *PNAS USA* 96:1339-1344 (1999).
Kozak "The scanning model for translation: an update" *J. Cell Biol.* 108:229-241 (1989).
Kozak "Point mutations close to the AUG initiator codon affect the efficiency of translation of rat preproinsulin in vivo" *Nature* 308, 241-246 USA (1984).
Mauro et al. "Antisense masking reveals contributions of mRNA-rRNA base pairing to translation of GTX and FGF2 mRNAs" *JBC* 283(48):33087-33093 (2008).
Meijer et al. "Translational control of the *Xenopus laevis* connexin-41 5'-untranslated region by three upstream open reading frames" *JBC* 275(40):30787-30793 (2000).
Owens et al. "Identification of two short internal ribosome entry sites selected from libraries of random oligonucleotides" *PNAS* 98(4):1471-1476 (2001).
Peabody "Translation initiation at an ACG triplet in mammalian cells" *JBC* 262(24):11847-11851 (1987).
Peabody "Translation initiative at non-AUG triplets in mammalian cells" *JBC* 264(9):5031-5035 (1989).
Dale, et al., "Improving protein solubility through rationally designed amino acid replacements: solubilization of the trimethoprim-resistant type S1 dihydrofolate reductase", *Protein Eng.* Jul. 1994; 7 (7):933-9.
Pullikotil, et al., "The Proprotein Convertase SKI-1/S1P", The Journal of Biological Chemistry, vol. 282, No. 37, pp. 27402-27413, Sep. 14, 2007, DOI 10.1074/jbc.M703200200.
Chapell et al. "Ribosomal Tethering and Clustering as Mechanisms for Translation Initiation." *PNAS*. 103.48(2006):18077-18082.
Mature miRNAs Search, miRBase, Retrieved from the Internet: Jul. 12, 2012. http://www.mirbase.orq/search.shtml, 2 pages.

* cited by examiner

REENGINEERING MRNA PRIMARY STRUCTURE FOR ENHANCED PROTEIN PRODUCTION

REFERENCE TO PRIORITY DOCUMENT

This application claims the benefit of priority under 35 U.S.C. §119(e) of U.S. Provisional Application Ser. No. 61/155,049, filed Feb. 24, 2009, entitled "Reengineering mRNA Primary Structure for Enhanced Protein Production." The subject matter of the above-noted application is incorporated by reference in its entirety by reference thereto.

INCORPORATION BY REFERENCE

The contents of the text file named "37651-503001WO Sequence listing.txt" which was created on Oct. 26, 2011 and is 53 KB in size, are hereby incorporated by reference in their entirety.

BACKGROUND

Translation initiation in eukaryotes involves recruitment by mRNAs of the 40S ribosomal subunit and other components of the translation machinery at either the 5' cap-structure or an internal ribosome entry site (IRES). Following its recruitment, the 40S subunit moves to an initiation codon. One widely held notion of translation initiation postulates that the 40S subunit moves from the site of recruitment to the initiation codon by scanning through the 5' leader in a 5' to 3' direction until the first AUG codon that resides in a good nucleotide context is encountered (Kozak "The Scanning Model for Translation: An Update" *J. Cell Biol.* 108:229-241 (1989)). More recently, it has been postulated that translation initiation does not involve scanning, but may involve tethering of ribosomal subunits at either the cap-structure or an IRES, or clustering of ribosomal subunits at internal sites (Chappell et al. "Ribosomal shunting mediated by a translational enhancer element that base pairs to 18S rRNA" *PNAS USA* 103(25):9488-9493 (2006); Chappell et al., "Ribosomal tethering and clustering as mechanisms for translation initiation" *PNAS USA* 103(48):18077-82 (2006)). The 40S subunit moves to an accessible AUG codon that is not necessarily the first AUG codon in the mRNA. Once the subunit reaches the initiation codon by whatever mechanism, the initiator Methionine-tRNA, which is associated with the subunit, base-pairs to the initiation codon, the large (60S) ribosomal subunit attaches, and peptide synthesis begins.

Inasmuch as translation is generally thought to initiate by a scanning mechanism, the effects on translation of AUG codons contained within 5' leaders, termed upstream AUG codons, have been considered, and it is known that an AUG codon in the 5' leader can have either a positive or a negative effect on protein synthesis depending on the gene, the nucleotide context, and cellular conditions. For example, an upstream AUG codon can inhibit translation initiation by diverting ribosomes from the authentic initiation codon. However, the notion that translation initiates by a scanning mechanism does not consider the effects of potential initiation codons in coding sequences on protein synthesis. In contrast, the tethering/clustering mechanisms of translation initiation suggests that putative initiation codons in coding sequences, which include both AUG codons and non-canonical codons, may be utilized, consequentially lowering the rate of protein synthesis by competing with the authentic initiation codon for ribosomes.

Micro RNA (miRNA)-mediated down-regulation can also negatively impact translation efficiency. miRNAs are generally between 21-23 nucleotides in length and are components of ribonucleoprotein complexes. It has been suggested that miRNAs can negatively impact protein levels by base-pairing to mRNAs and reducing mRNA stability, nascent peptide stability and translation efficiency (Eulalio et al. "Getting to the Root of miRNA-Mediated Gene Silencing" *Cell* 132:9-14 (1998)). Although miRNAs generally mediate their effects by base-pairing to binding sites in the 3' untranslated sequences (UTRs) of mRNAs, they have been shown to have similar repressive effects from binding sites contained within coding sequences and 5' leader sequences. Base-pairing occurs via the so-called "seed sequence," which includes nucleotides 2-8 of the miRNA. There may be more than 1,000 different miRNAs in humans.

The negative impact of putative initiation codons in mRNA coding sequences and miRNA-binding sites in mRNAs pose challenges to the pharmaceutical industry. For example, the industrial production of protein drugs, DNA vaccines for antigen production, general research purposes and for gene therapy applications are all affected by a sub-optimal rate of protein synthesis or sequence stability. Improving protein yields and higher protein concentration can minimize the costs associated with industrial scale cultures, reduce costs of producing drugs and can facilitate protein purification. Poor protein expression limits the large-scale use of certain technologies, for example, problems in expressing enough antigen from a DNA vaccine to generate an immune response to conduct a phase 3 clinical trial.

SUMMARY

There is a need in the art for improving the efficiency and stability of protein translation and improving protein yield and concentration, for example, in the industrial production of protein drugs.

Disclosed is a method of improving full-length protein expression efficiency. The method includes providing a polynucleotide having a coding sequence for the protein; a primary initiation codon that is upstream of the coding sequence; and one or more secondary initiation codons located within the coding sequence. The method also includes mutating one or more secondary initiation codons resulting in a decrease in initiation of protein synthesis at the one or more secondary initiation codons resulting in a reduction of ribosomal diversion away from the primary initiation codon, thereby increasing full-length protein expression efficiency.

The method can also include mutating one or more nucleotides such that the amino acid sequence remains unaltered. The one or more secondary initiation codons can be in the same reading frame as the coding sequence or out-of-frame with the coding sequence. The one or more secondary initiation codons can be located one or more nucleotides upstream or downstream from a ribosomal recruitment site. The ribosomal recruitment site can include a cap or an IRES. The one or more secondary initiation codons can be selected from AUG, ACG, GUG, UUG, CUG, AUA, AUC, and AUU. The method can include mutating more than one secondary initiation codon within the coding sequence. The method can include mutating all the secondary initiation codons within the coding sequence. A flanking nucleotide can be mutated to a less favorable nucleotide context. The mutation of the one or more secondary initiation codons can avoid introducing new initiation codons. The mutation of the one or more secondary initiation codons can avoid introducing miRNA seed sequences. The mutation of the one or more secondary initiation codons can avoid altering usage bias of mutated codons. The generation of truncated proteins, polypeptide, or peptides other than the full-length encoded protein can be reduced. Mutating one or more secondary initiation codons can avoid introducing miRNA seed sequences, splice donor or acceptor sites, or mRNA destabilization elements.

Also disclosed is a method of improving full-length protein expression efficiency. The method includes providing a polynucleotide sequence having a coding sequence for the protein and one or more miRNA binding sites located within the coding sequence; and mutating the one or more miRNA binding sites. The mutation results in a decrease in miRNA binding at the one or more miRNA binding sites resulting in a reduction of miRNA-mediated down regulation of protein translation, thereby increasing full-length protein expression efficiency.

The method can also include mutating one or more nucleotides such that the amino acid sequence remains unaltered. The method can include mutating one or more nucleotides in an miRNA seed sequence. The method can include mutating one or more nucleotides such that initiation codons are not introduced into the polynucleotide sequence. The method can include mutating one or more nucleotides such that rare codons are not introduced into the polynucleotide sequence. The method can include mutating one or more nucleotides such that additional miRNA seed sequences are not introduced into the polynucleotide sequence. The one or more miRNA binding sites can be located within the coding sequence. The one or more miRNA binding sites can be located within the 3' untranslated region. The one or more miRNA binding sites can be located within the 5' leader sequence.

A further understanding of the nature and advantages of the present disclosure may be realized by reference to the remaining portions of the specification and claims.

DETAILED DESCRIPTION

I. Overview

Figure 1A:
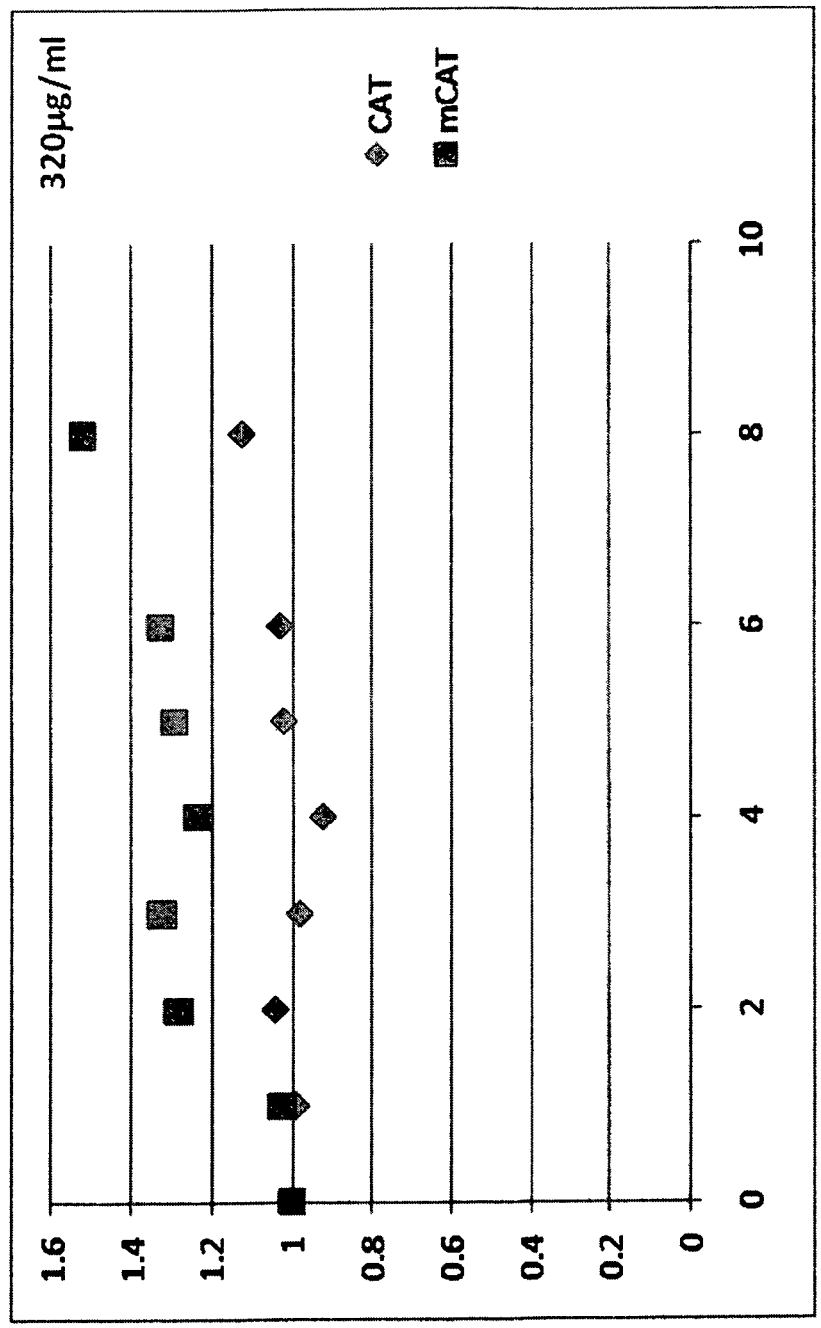
FIGS. 1A-1B show growth curves of *E. coli* DH5α cell cultures transformed with CAT (diamonds) or mCAT expression constructs (squares)

Described herein are methods to modify natural mRNAs or to engineer synthetic mRNAs to increase levels of the encoded protein. These rules describe modifications to mRNA coding and 3' UTR sequences intended to enhance protein synthesis by: 1) decreasing ribosomal diversion via AUG or non-canonical initiation codons in coding sequences, and/or 2) by evading miRNA-mediated down-regulation by eliminating miRNA binding sites in coding sequences.

Described are methods of reengineering mRNA primary structure that can be used to increase the yield of specific proteins in eukaryotic and bacterial cells. The methods described herein can be applied to the industrial production of protein drugs as well as for research purposes, gene therapy applications, and DNA vaccines for increasing antigen production. Greater protein yields minimize the costs associated with industrial scale cultures and reduce drug costs. In addition, higher protein concentrations can facilitate protein purification. Moreover, processes that may otherwise not be possible due to poor protein expression, e.g. in the conduct of phase 3 clinical trials, or in expressing enough antigen from a DNA vaccine to generate an immune response can be possible using the methods described herein.

II. Definitions

This specification is not limited to the particular methodology, protocols, and reagents described, as these may vary. It is also to be understood that the terminology used herein is for the purpose of describing particular embodiments only, and is not intended to limit the scope of the present methods which will be described by the appended claims.

As used herein, the singular forms "a", "an", and "the" include plural reference unless the context clearly dictates otherwise. Thus, for example, reference to "a cell" includes a plurality of such cells, reference to "a protein" includes one or more proteins and equivalents thereof known to those skilled in the art, and so forth.

Unless defined otherwise, all technical and scientific terms used herein have the same meaning as commonly understood by those of ordinary skill in the art to which this disclosure pertains. The following references provide one of skill with a general definition of many of the terms used in this disclosure: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). Further clarifications of some of these terms as they apply specifically to this disclosure are provided herein.

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "cistron" means a unit of DNA that encodes a single polypeptide or protein. The term "transcriptional unit" refers to the segment of DNA within which the synthesis of RNA occurs.

The term "DNA vaccines" refers to a DNA that can be introduced into a host cell or a tissue and therein expressed by cells to produce a messenger ribonucleic acid (mRNA) molecule, which is then translated to produce a vaccine antigen encoded by the DNA.

The language "gene of interest" is intended to include a cistron, an open reading frame (ORF), or a polynucleotide sequence which codes for a protein product (protein of interest) whose production is to be modulated. Examples of genes of interest include genes encoding therapeutic proteins, nutritional proteins and industrial useful proteins. Genes of interest can also include reporter genes or selectable marker genes such as enhanced green fluorescent protein (EGFP), luciferase genes (*Renilla* or *Photinus*).

Expression is the process by which a polypeptide is produced from DNA. The process involves the transcription of the gene into mRNA and the subsequent translation of the mRNA into a polypeptide.

The term "endogenous" as used herein refers to a gene normally found in the wild-type host, while the term "exogenous" refers to a gene not normally found in the wild-type host.

A "host cell" refers to a living cell into which a heterologous polynucleotide sequence is to be or has been introduced. The living cell includes both a cultured cell and a cell within a living organism. Means for introducing the heterologous polynucleotide sequence into the cell are well known, e.g., transfection, electroporation, calcium phosphate precipitation, microinjection, transformation, viral infection, and/or the like. Often, the heterologous polynucleotide sequence to be introduced into the cell is a replicable expression vector or cloning vector. In some embodiments, host cells can be engineered to incorporate a desired gene on its chromosome or in its genome. Many host cells that can be employed in the practice of the present methods (e.g., CHO cells) serve as hosts are well known in the art. See, e.g., Sambrook et al., *Molecular Cloning: A Laboratory Manual*, Cold Spring Harbor Press (3$^{rd}$ ed., 2001); and Brent et al., *Current Protocols in Molecular Biology*, John Wiley & Sons, Inc. (Ringbou ed., 2003). In some embodiments, the host cell is a eukaryotic cell.

The term "inducing agent" is used to refer to a chemical, biological or physical agent that effects translation from an inducible translational regulatory element. In response to exposure to an inducing agent, translation from the element generally is initiated de novo or is increased above a basal or constitutive level of expression. An inducing agent can be, for example, a stress condition to which a cell is exposed, for example, a heat or cold shock, a toxic agent such as a heavy metal ion, or a lack of a nutrient, hormone, growth factor, or the like; or can be a compound that affects the growth or differentiation state of a cell such as a hormone or a growth factor.

The phrase "isolated or purified polynucleotide" is intended to include a piece of polynucleotide sequence (e.g., DNA) which has been isolated at both ends from the sequences with which it is immediately contiguous in the naturally occurring genome of the organism. The purified polynucleotide can be an oligonucleotide which is either double or single stranded; a polynucleotide fragment incorporated into a vector; a fragment inserted into the genome of a eukaryotic or prokaryotic organism; or a fragment used as a probe. The phrase "substantially pure," when referring to a polynucleotide, means that the molecule has been separated from other accompanying biological components so that, typically, it has at least 85 percent of a sample or greater percentage.

The term "nucleotide sequence," "nucleic acid sequence," "nucleic acid," or "polynucleotide sequence," refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

The term "promoter" means a nucleic acid sequence capable of directing transcription and at which transcription is initiated. A variety of promoter sequences are known in the art. For example, such elements can include, but are not limited to, TATA-boxes, CCAAT-boxes, bacteriophage RNA polymerase specific promoters (e.g., T7, SP6, and T3 promoters), an SP1 site, and a cyclic AMP response element. If the promoter is of the inducible type, then its activity increases in response to an inducing agent.

The five prime leader or untranslated region (5' leader, 5' leader sequence or 5' UTR) is a particular section of messenger RNA (mRNA) and the DNA that codes for it. It starts at the +1 position (where transcription begins) and ends just before the start codon (typically AUG) of the coding region. In bacteria, it may contain a ribosome binding site (RBS) known as the Shine-Delgarno sequence. 5' leader sequences range in length from no nucleotides (in rare leaderless messages) up to >1,000-nucleotides. 3' UTRs tend to be even longer (up to several kilobases in length).

The term "operably linked" or "operably associated" refers to functional linkage between genetic elements that are joined in a manner that enables them to carry out their normal functions. For example, a gene is operably linked to a promoter when its transcription is under the control of the promoter and the transcript produced is correctly translated into the protein normally encoded by the gene. Similarly, a translational enhancer element is operably associated with a gene of interest if it allows up-regulated translation of a mRNA transcribed from the gene.

A sequence of nucleotides adapted for directional ligation, e.g., a polylinker, is a region of an expression vector that provides a site or means for directional ligation of a polynucleotide sequence into the vector. Typically, a directional polylinker is a sequence of nucleotides that defines two or more restriction endonuclease recognition sequences, or restriction sites. Upon restriction cleavage, the two sites yield cohesive termini to which a polynucleotide sequence can be ligated to the expression vector. In an embodiment, the two restriction sites provide, upon restriction cleavage, cohesive termini that are non-complementary and thereby permit directional insertion of a polynucleotide sequence into the cassette. For example, the sequence of nucleotides adapted for directional ligation can contain a sequence of nucleotides that defines multiple directional cloning means. Where the sequence of nucleotides adapted for directional ligation defines numerous restriction sites, it is referred to as a multiple cloning site.

The term "subject" for purposes of treatment refers to any animal classified as a mammal, e.g., human and non-human mammals. Examples of non-human animals include dogs, cats, cattle, horses, sheep, pigs, goats, rabbits, and etc. Except when noted, the terms "patient" or "subject" are used herein interchangeably. In an embodiment, the subject is human.

Transcription factor refers to any polypeptide that is required to initiate or regulate transcription. For example, such factors include, but are not limited to, c-Myc, c-Fos, c-Jun, CREB, cEts, GATA, GAL4, GAL4/Vp16, c-Myb, MyoD, NF-κB, bacteriophage-specific RNA polymerases, Hif-1, and TRE. Example of sequences encoding such factors include, but are not limited to, GenBank accession numbers K02276 (c-Myc), K00650 (c-fos), BC002981 (c-jun), M27691 (CREB), X14798 (cEts), M77810 (GATA), K01486 (GAL4), AY136632 (GAL4/Vp16), M95584 (c-Myb), M84918 (MyoD), 2006293A (NF-κB), NP 853568 (SP6 RNA polymerase), AAB28111 (T7 RNA polymerase), NP 523301 (T3 RNA polymerase), AF364604 (HIF-1), and X63547 (TRE).

A "substantially identical" nucleic acid or amino acid sequence refers to a nucleic acid or amino acid sequence which includes a sequence that has at least 90% sequence identity to a reference sequence as measured by one of the well known programs described herein (e.g., BLAST) using standard parameters. The sequence identity can be at least 95%, at least 98%, and at least 99%. In some embodiments, the subject sequence is of about the same length as compared to the reference sequence, i.e., consisting of about the same number of contiguous amino acid residues (for polypeptide sequences) or nucleotide residues (for polynucleotide sequences).

Sequence identity can be readily determined with various methods known in the art. For example, the BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "treating" or "alleviating" includes the administration of compounds or agents to a subject to prevent or delay the onset of the symptoms, complications, or biochemical indicia of a disease (e.g., a cardiac dysfunction), alleviating the symptoms or arresting or inhibiting further development of the disease, condition, or disorder. Subjects in need of treatment include patients already suffering from the disease or disorder as well as those prone to have the disorder or those in whom the disorder is to be prevented.

Treatment may be prophylactic (to prevent or delay the onset of the disease, or to prevent the manifestation of clinical or subclinical symptoms thereof) or therapeutic suppression or alleviation of symptoms after the manifestation of the disease. In the treatment of cardiac remodeling and/or heart failure, a therapeutic agent may directly decrease the pathology of the disease, or render the disease more susceptible to treatment by other therapeutic agents.

The term "vector" or "construct" refers to polynucleotide sequence elements arranged in a definite pattern of organization such that the expression of genes/gene products that are operably linked to these elements can be predictably controlled. Typically, they are transmissible polynucleotide sequences (e.g., plasmid or virus) into which a segment of foreign DNA can be spliced in order to introduce the foreign DNA into host cells to promote its replication and/or transcription.

A cloning vector is a DNA sequence (typically a plasmid or phage) which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain one or more markers suitable for use in the identification of transformed cells. For example, markers may provide tetracycline or ampicillin resistance.

An expression vector is similar to a cloning vector but is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

An "initiation codon" or "initiation triplet" is the position within a cistron where protein synthesis starts. It is generally located at the 5' end of the coding sequence. In eukaryotic mRNAs, the initiation codon typically consists of the three nucleotides (the Adenine, Uracil, and Guanine (AUG) nucleotides) which encode the amino acid Methionine (Met). In bacteria, the initiation codon is also typically AUG, but this codon encodes a modified Methionine (N-Formylmethionine (fMet)). Nucleotide triplets other than AUG are sometimes used as initiation codons, both in eukaryotes and in bacteria.

A "downstream initiation codon" refers to an initiation codon that is located downstream of the authentic initiation codon, typically in the coding region of the gene. An "upstream initiation codon" refers to an initiation codon that is located upstream of the authentic initiation codori in the 5' leader region.

As used herein, reference to "downstream" and "upstream" refers to a location with respect to the authentic initiation codon. For example, an upstream codon on an mRNA sequence is a codon that is towards the 5'-end of the mRNA sequence relative to another location within the sequence (such as the authentic initiation codon) and a downstream codon refers to a codon that is towards the 3'-end of the mRNA sequence relative to anther location within the sequence.

As used herein, "authentic initiation codon" or "primary initiation codon" refers to the initiation codon of a cistron that encodes the first amino acid of the coding sequence of the encoded protein of interest whose production is to be modulated. A "secondary initiation codon" refers to an initiation codon that is other than the primary or authentic initiation codon for the encoded protein of interest. The secondary initiation codon is generally downstream of the primary or authentic initiation codon and located within the coding sequence.

As used herein, "increased protein expression" refers to translation of a modified mRNA where one or more secondary initiation codons are mutated that generates polypeptide concentration that is at least about 5%, 10%, 20%, 30%, 40%, 50% or greater over the polypeptide concentration obtained from the wild type mRNA where the one or more secondary initiation codons have not been mutated. Increased protein expression can also refer to protein expression of a mutated mRNA that is 1.5-fold, 2-fold, 3-fold, 5-fold, 10-fold or more over the wild type mRNA.

As used herein, "ribosomal recruitment site" refers to a site within an mRNA to which a ribosome subunit associates prior to initiation of translation of the encoded protein. Ribosomal recruitment sites can include the cap structure, a modified nucleotide ($m^7G$ cap-structure) found at the 5' ends of mRNAs, and sequences termed internal ribosome entry sites (IBES), which are contained within mRNAs. Other ribosomal recruitment sites can include a 9-nucleotide sequence from the Gtx homeodomain mRNA. The ribosomal recruitment site is often upstream of the authentic initiation codon, but can also be downstream of the authentic initiation codon.

As used herein, "usage bias" refers to the particular preference an organism shows for one of the several codons that encode the same amino acid. Altering usage bias refers to mutations that lead to use of a different codon for the same amino acid with a higher or lower preference than the original codon.

As used herein, "full-length protein" refers to a protein which encompasses essentially every amino acid encoded by the gene encoding the protein. Those of skill in the art know there are subtle modifications of some proteins in living cells so that the protein is actually a group of closely related proteins with slight alterations. For example, some but not all proteins a) have amino acids removed from the amino-terminus, and/or b) have chemical groups added which could increase molecular weight. Most bacterial proteins as encoded contain a methionine and an alanine residue at the amino-terminus of the protein; one or both of these residues are frequently removed from active forms of the protein in the bacterial cell. These types of modifications are typically heterogenous so not all modifications happen to every molecule. Thus, the natural "full-length" molecule is actually a family of molecules that start from the same amino acid sequence but have small differences in how they are modified. The term "full-length protein" encompasses such a family of molecules.

As used herein, "rescued" or "modified" refer to nucleotide alterations that remove most to all secondary initiation codons from the coding region. "Partially modified" refers to nucleotide alterations that remove a subset of all possible mutations of secondary initiation codons from the coding region.

III. Reduction of Ribosomal diversion via downstream initiation codons

As mentioned above, it is well-known that features contained within 5' leaders can affect translation efficiency. For example, an AUG codon in the 5' leader, termed an upstream AUG codon, can have either a positive or a negative effect on protein synthesis depending on the gene, the nucleotide context, and cellular conditions. An upstream AUG codon can inhibit translation initiation by diverting ribosomes from the authentic initiation codon (Meijer et al., "Translational Control of the *Xenopus laevis* Connexin-41 5'-Untranslated Region by Three Upstream Open Reading Frames" *J. Biol. Chem.* 275(40):30787-30793 (2000)). For example, FIGS. 6 and 8 in Meijer et al. show the ribosomal diversion effect of upstream AUG codon in the 5' leader sequence.

Although AUG/ATG is the usual translation initiation codon in many species, it is known that translation can sometimes also initiate at other upstream codons, including ACG, GUG/GTG, UUG/TTG, CUG/CTG, AUA/ATA, AUC/ATC, and AUU/ATT in vivo. For example, it has been shown that mammalian ribosomes can initiate translation at a non-AUG triplet when the initiation codon of mouse dihydrofolate reductase (dhfr) was mutated to ACG (Peabody, D. S. (1987) *J. Biol. Chem.* 262, 11847-11851). A further study by Peabody showed that mutant initiation codons AUG of dhfr (GUG, UUG, CUG, AUA, AUC and AUU) all were able to direct the synthesis of apparently normal dhfr (Peabody, D. S. (1989) *J. Biol. Chem.* 264, 5031-5035).

The tethering and clustering models of translation initiation postulate that translation can initiate at an accessible initiation codon and studies have shown that an initiation codon can be used in a distance-dependent manner downstream of the ribosomal recruitment site (cap or IRES) (Chappell et al. "Ribosomal tethering and clustering as mechanisms for translation initiation" *PNAS USA* 103(48):18077-82 2006). This suggests that putative initiation codons in coding sequences may also be utilized. Translation initiation at downstream initiation codons, or secondary initiation sites, can compete with the authentic initiation codon, or primary initiation site, for ribosomes and lower the expression of the encoded protein. Decreasing the availability of these secondary initiation sites, such as by mutating them into a non-initiation codon, increases the availability of the primary initiation sites to the ribosome and a more efficient encoded protein expression.

The present method allows for improved and more efficient protein expression and reduces the competition between various initiation codons for the translation machinery. By eliminating downstream initiation codons in coding sequences that are in the same reading frame as the encoded protein, the generation of truncated proteins, with potential altered function, will be eliminated. In addition, by eliminating downstream initiation codons that are out-of-frame with the coding sequence, the generation of various peptides, some of which may have negative effects on cell physiology or protein production, will also be eliminated. This advantage can be particularly important for applications in DNA vaccines or gene therapy.

Direct mutation of downstream initiation codons can take place such that the encoded amino acid sequence remains unaltered. This is possible in many cases because the genetic code is degenerate and most amino acids are encoded by two or more codons. The only exceptions are Methionine and Tryptophan, which are only encoded by one codon, AUG, and UGG, respectively. Mutation of a downstream initiation codon that also alters the amino acid sequence can also be considered. In such cases, the effects of altering the amino acid sequence can be evaluated. Alternatively, if the amino acid sequence is to remain unaltered, the nucleotides flanking the putative initiation codon can sometimes be mutated to diminish the efficiency of the initiation codon. For AUG codons, this can be done according to the nucleotide context rules established by Marilyn Kozak (Kozak, M. (1984) *Nature* 308, 241-246), which state that an AUG in excellent context contains a purine at position −3 and a G at +4, where AUG is numbered +1, +2, +3.

For non-AUG codons, similar rules seem to apply with additional determinants from nucleotides at positions +5 and +6. In designing mutations, the codon usage bias can, in many cases, remain relatively unaltered, e.g. by introducing mutated codons with similar codon bias as the wild type codon. Inasmuch as different organisms have different codon usage frequencies, the specific mutations for expression in cells from different organisms will vary accordingly.

It should be appreciated that the methods disclosed herein are not limited to eukaryotic cells, but also apply to bacteria. Although bacterial translation initiation is thought to differ from eukaryotes, ribosomal recruitment still occurs via cis-elements in mRNAs, which include the so-called Shine-Delgarno sequence. Non-AUG initiation codons in bacteria include ACG, GUG, UUG, CUG, AUA, AUC, and AUU.

In an embodiment, disclosed are modifications to coding sequences that enhance protein synthesis by decreasing ribosomal diversion via downstream initiation codons. These codons can include AUG/ATG and other nucleotide triplet codons known to function as initiation codons in cells, including but not limited to ACG, GUG/GTG, UUG/TTG, CUG/CTG, AUA/ATA, AUC/ATC, and AUU/ATT. In one embodiment the downstream initiation codon is mutated. Reengineering of mRNA coding sequences to increase protein production can involve mutating all downstream initiation codons or can involve mutating just some of the downstream initiation codons. In another embodiment, the flanking nucleotides are mutated to a less favorable nucleotide context. In an embodiment, ATG codons in the signal peptide can be mutated to ATC codons resulting in a Methionine to Isoleucine substitution. In another embodiment, CTG codons in the signal peptide can be mutated to CTC. In another embodiment, ATG codons can be mutated to ATC codons resulting in a Methionine (M) to Isoleucine (I) amino acid substitution, and CTG codons can be mutated to CTCs. In another embodiment, ATG codons can be mutated to ATC codons, CTG codons can be mutated to CTC codons, and the context of initiator AUG can be improved by changing the codon 3' of the initiator from CCC to GCT resulting in a Proline (P) to Argenine (R) amino acid substitution. In other embodiments, modifications can be made to the signal peptide in which one or more AUG and CUG codons can be removed. Modifications can be made including a modified signal peptide by removal of most of the potential initiation codons, removal of ATG and CTGs of the signal peptide, removal of ATG, CTG and ACG codons resulting in a Glutamic acid (E) to Glutamine (Q) amino acid substitution or a Histidine (H) to Argenine (R) amino acid substitution.

Standard techniques in molecular biology can be used to generate the mutated nucleic acid sequences. Such techniques include various nucleic acid manipulation techniques, nucleic acid transfer protocols, nucleic acid amplification protocols and other molecular biology techniques known in the art. For example, point mutations can be introduced into a gene of interest through the use of oligonucleotide mediated site-directed mutagenesis. Modified sequences also can be generated synthetically by using oligonucleotides synthesized with the desired mutations. These approaches can be used to introduce mutations at one site or throughout the coding region. Alternatively, homologous recombination can be used to introduce a mutation or exogenous sequence into a target sequence of interest. Nucleic acid transfer protocols include calcium chloride transformation/transfection, electroporation, liposome mediated nucleic acid transfer, N-[1-(2,3-Dioloyloxy)propyl]-N,N,N-trimethylammonium methylsulfate meditated transformation, and others. In an alternative mutagenesis protocol, point mutations in a particular gene can also be selected for using a positive selection pressure. See, e.g., Current Techniques in Molecular Biology, (Ed. Ausubel, et al.). Nucleic acid amplification protocols include but are not limited to the polymerase chain reaction (PCR). Use of nucleic acid tools such as plasmids, vectors, promoters and other regulating sequences, are well known in the art for a large variety of viruses and cellular organisms. Further a large variety of nucleic acid tools are available from many different sources including ATCC, and various commercial sources. One skilled in the art will be readily able to select the appropriate tools and methods for genetic modifications of any particular virus or cellular organism according to the knowledge in the art and design choice. Protein expression can be measured also using various standard methods. These include, but are not limited to, Western blot analysis, ELISA, metabolic labeling, and enzymatic activity measurements.

IV. Evasion of miRNA-Mediated Down-Regulation

MicroRNAs are an abundant class of small noncoding RNAs that generally function as negative gene regulators. In an embodiment, modifications can be made to mRNA sequences, including 5' leader, coding sequence, and 3' UTR, to evade miRNA-mediated down-regulation. Such modification can thereby alter mRNA or nascent peptide stability, and enhance protein synthesis and translation efficiency.

MiRNAs can be generally between 21-23 nucleotide RNAs that are components of ribonucleoprotein complexes. miRNAs can affect mRNA stability or protein synthesis by base-pairing to mRNAs. miRNAs generally mediate their effects by base-pairing to binding sites in the 3' UTRs of mRNAs. However, they have been shown to have similar repressive effects from binding sites contained within coding sequences and 5' leader sequences. Base-pairing occurs via the so-called "seed sequence," which consists of nucleotides 2-8 of the miRNA. There may be more than 1,000 different miRNAs in humans.

Reengineering mRNAs to circumvent miRNA-mediated repression can involve mutating all seed sequences within an mRNA. As with the initiation codon mutations described above, these mutations can ensure that the encoded amino acid sequence remains unaltered, and act not to introduce initiation codons, rare codons, or other miRNA seed sequences.

A computer program can be used to reengineer mRNA sequences according to a cell type of interest, e.g. rodent cells for expression in Chinese hamster ovary cells, or human cells for expression in human cell lines or for application in DNA vaccines. This program can recode an mRNA to eliminate potential initiation codons except for the initiation codon. In the case of in-frame AUG codons in the coding sequence, the context of these downstream initiation codons can be weakened if possible. Mutations can be performed according to the codon bias for the cell line of interest, e.g. human codon bias information can be used for human cell lines, *Saccharomyces cerevisiae* codon bias information can be used for this yeast, and *E.coli* codon bias information can be used for this bacteria. In higher eukaryotic mRNAs, the recoded mRNA can then be searched for all known seed sequences in the organism of interest, e.g. human seed sequences for human cell lines. Seed sequences can be mutated with the following considerations: 1) without disrupting the amino acid sequence, 2) without dramatically altering the usage bias of mutated codons, 3) without introducing new putative initiation codons.

While this specification contains many specifics and described with references to preferred embodiments thereof, these should not be construed as limitations on the scope of a method that is claimed or of what may be claimed, but rather as descriptions of features specific to particular embodiments. It will be understood by those skilled in the art that various changes in form and details may be made therein without departing from the meaning of the subject matter described. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. The scope of the subject matter is defined by the claims that follow.

All publications, databases, GenBank sequences, patents, and patent applications cited in this specification are herein incorporated by reference as if each was specifically and individually indicated to be incorporated by reference.

EXAMPLES

The following examples are provided as further illustration, but not to limit the scope. Other variants will be readily apparent to one of ordinary skill in the art and are encompassed by the appended claims.

Example 1

Modification of Multiple Translation Initiation Sites within mRNA Transcripts The presence of multiple translation initiation sites within the 5'-UTR and coding regions of mRNA transcripts decreases translation efficiency by, for example, diverting ribosomes from the authentic or demonstrated translation initiator codon. Alternatively, or in addition, the presence of multiple translation initiation sites downstream of the authentic or demonstrated translation initiator codon induces initiation of translation of one or more protein isoforms that reduce the translation efficiency of the full length protein. To improve translation efficiency of mRNA transcripts encoding commercially-valuable human proteins, potential translation initiation sites within all reading frames upstream and downstream of the authentic or demonstrated translation initiator codon are mutated to eliminate these sites. In preferred aspects of this method, the mRNA sequence is altered but the resultant amino acid encoded remains the same. Alternatively, conservative changes are induced that substitute amino acids having similar physical properties.

The canonical translation initiation codon is AUG/ATG. Other identified initiator codons include, but are not limited to, ACG, GUG/GTG, UUG/TTG, CUG/CTG, AUA/ATA, AUC/ATC, and AUU/ATT.

Intracellular Protein: Chloramphenicol Acetyl Transferase (CAT)

Chloramphenicol is an antibiotic that interferes with bacterial protein synthesis by binding the 50S ribosomal subunit and preventing peptide bond formation. The resistance gene (cat) encodes an acetyl transferase enzyme that acetylates and thereby inactivates this antibiotic by acetylating the drug at one or both of its two hydroxyl groups. The unmodified open reading frame of CAT contains 113 potential initiation codons (20 ATG, including the authentic initiation codon, 8 ATC, 8 ACG, 12 GTG, 8 TTG, 11 CTG, 6 AGG, 10 AAG, 16 ATA, and 14 ATT codons) (SEQ ID NO: 120). SEQ ID NO: 121 is a fully modified CAT ORF and SEQ ID NO: 122 is a partially modified CAT ORFs in which only some of the potential modifications were made.

Figure 1B:
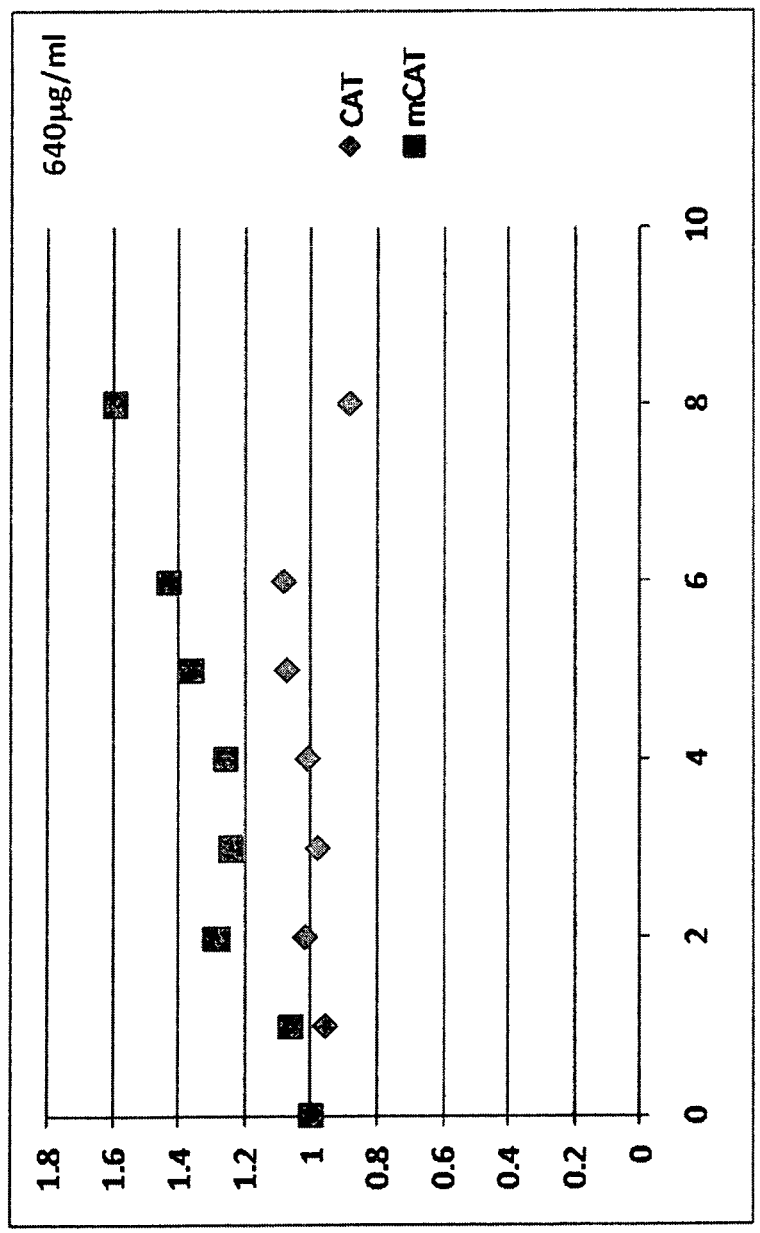

FIGS. 1A-1B show bacterial expression constructs were generated containing the CAT cistron (CAT) and a partially modified CAT cistron (mCAT) and tested in the *E. coli* bacterial strain DH5α. DH5α cells were transformed with the CAT and mCAT expression constructs and plated onto LB/ampicillin plates. Cultures were obtained from single colonies and cultured in LB/ampicillin (~50 μg/ml) at 37° C. with shaking at 220 rpm until logarithmic growth was reached as determined by measuring the $A_{600}$ of the culture. The cultures were then diluted with LB/ampicillin to comparable $A_{600}$'s. The $A_{600}$ of the culture derived from DH5α cells transformed with the CAT expression construct was 0.3, while that from the cells transformed with the mCAT expression construct was 0.25. Chloramphenicol acetyltransferase expression was induced via the lac operon contained within the CAT and mCAT plasmids by the introduction of Isopropyl β-D-1-thiogalactopyranoside (IPTG, final concentration of 0.4mM). Three milliliters of each culture was transferred to a fresh tube containing chloramphenicol resulting in a final concentration of 20, 40, 80, 160, 320, 640, 1280, and 2560μg/ml. Cultures were incubated at 37° C. with shaking at 220 rpm and the $A_{600}$ of each culture measured at 1 hour intervals.

FIGS. 1A-1B show growth curves of cultures of DH5α cells transformed with CAT (diamonds) and mCAT (squares) expression constructs. Chloramphenicol acetyltransferase expression was induced by the addition of IPTG, (0.4 mM final concentration) 3 milliliters of IPTG containing culture was added to fresh tubes containing Chloramphenicol resulting in final concentrations of 0, 40, 80, 160, 320, 640, 1280, and 2560 μg/ml. Cultures were incubated at 37° C. with shaking at 220 rpm and the $A_{600}$ of each culture measured over time. The results for cultures grown in the presence of 320 and 640 μg/ml Chloramphenicol are shown. The X-axis represents time in hours, the Y-axis represents normalized $A_{600}$ (relative to starting $A_{600}$).

The results showed that bacteria transformed with the mCAT expression construct grew better than the bacteria transformed with the CAT expression construct at all concentrations. As shown in FIGS. 1A-1B, in high concentrations of Chloramphenicol (320 and 640 μg/ml), cells with the modified CAT still grew, but cells with the wild type CAT did not. These results indicate that more functional Chloramphenicol acetyltransferase enzyme was expressed from the mCAT construct thus allowing the bacteria transformed with this expression construct to grow better in the presence of this antibiotic.

Figure 2:
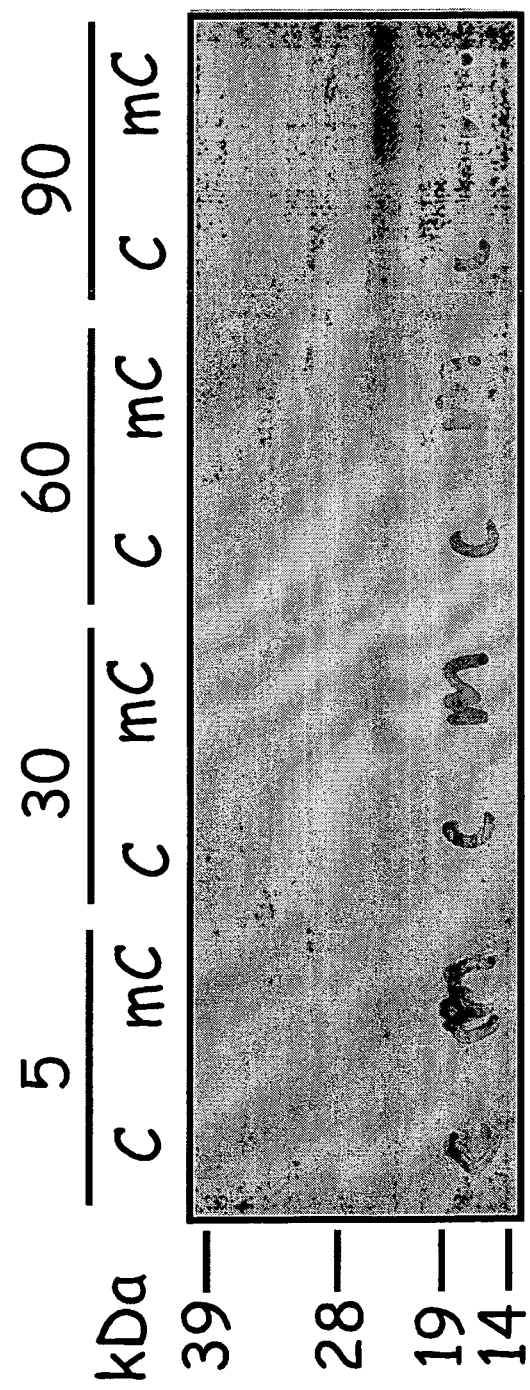
FIG. 2 shows a Western blot analysis of lysates collected from *E. coli* DH5α cells transformed with CAT (C) or mCAT (mC) expression constructs.

To determine the relative amounts of Chloramphenicol acetyltransferase enzyme synthesized from DH5α cells transformed with the CAT and mCAT expression constructs, Western blot analysis was performed on cell extracts at 5, 30, 60 and 90 minutes after induction by IPTG. 50 μl of culture at each time point was centrifuged, and bacterial pellets resuspended in 30 μl of TE buffer and 10 μl of a 4 ×SDS gel loading buffer. The sample was heated at 95° C. for 3 minutes and loaded onto a 10% Bis-Tris/SDS polyacylamide gel. Proteins were transferred to a PVDF membrane and probed with an anti-CAT antibody. FIG. 2 is a Western blot analysis of lysates from DH5α cells transformed with the CAT (C) and mCAT (mCAT) expression constructs at various times after IPTG induction. The results showed that the amount of Chloramphenicol acetyltransferase protein (above the 19 kDa marker) is substantially increased in DH5α cells transformed with the mCAT expression construct (mC) at all time points tested.

Analysis of the Chloramphenicol acetyltransferase ORF was also performed in mammalian cells. The CAT ORF and the partially modified CAT ORF were cloned into mammalian expression constructs containing a CMV promoter and tested by transient transfection into Chinese Hamster Ovary (DG44) cells. In brief, 0.5 μg of each expression construct along with 20 ng of a co-transfection control plasmid that expresses the β-galactosidase reporter protein (pCMβ, Clontech) was transfected into 100,000 DG44 cells using the Fugene 6 (Roche) transfection reagent according to the manufacturer's instructions. Twenty-four hours post transfection, cells were lysed using 250 μl of lysis buffer. Lac Z reporter assay was performed to ensure equal transfection efficiencies between samples. 30 μl of lysate was added to 10 μl of a 4×SDS gel loading buffer. The sample was heated at 72° C. for 10 minutes and loaded onto a 10% Bis-Tris/SDS polyacylamide gel. Proteins were transferred to a PVDF membrane and probed with an α-CAT antibody.

Figure 3:
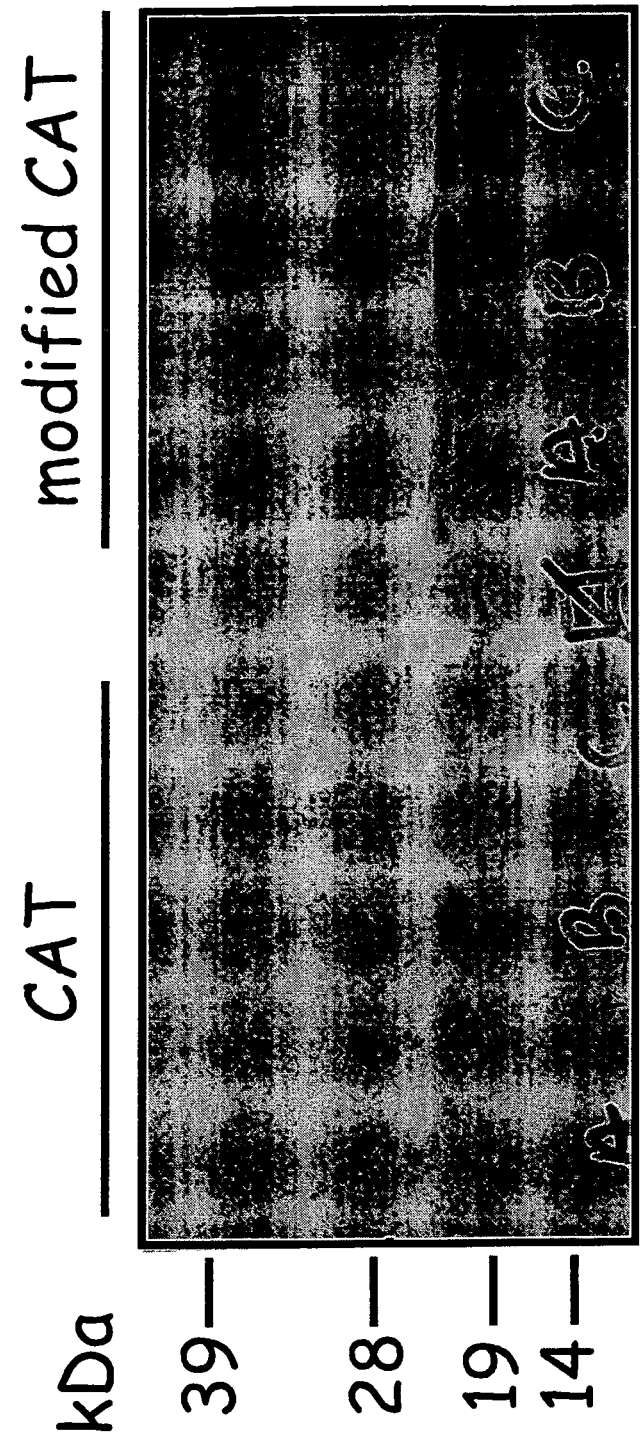
FIG. 3 shows a Western blot analysis of extracts from DG44 cells transformed with wild type CAT or modified CAT expression constructs.

FIG. 3 shows a Western blot analysis of extracts from the DG44 cells transformed with wild type (CAT) and modified CAT expression constructs. Cell extracts were fractionated on 10% Bis-Tris gels in 1×MOPS/SDS, transferred to PVDF membrane and probed with an anti-CAT antibody. Experiments were performed in triplicate with extracts from cells in which transfection efficiency was the same.

Comparisons were made between three transfections with the wild type (CAT) and three with the modified CAT. The amount of CAT protein (above the 19 kDa marker) is substantially increased in cells transfected with the modified construct. The results showed that the amount of CAT protein (above the 19 kDa marker) is substantially increased in DG44 cells transfected with the mCAT construct. Modification of the CAT ORF by eliminating multiple translation initiation sites within the resulting mRNA transcripts demonstrated that this technology may be of practical use in numerous organisms besides just mammalian and bacterial cells.

Secreted Proteins

The usefulness of this technology was also investigated with secreted proteins. Mammalian expression constructs were generated for a signal peptide that is encoded within the Homo sapiens CD5 molecule (CD5), mRNA. Mammalian expression constructs were generated in which transcription was driven by a CMV promoter and where the cd5 signal peptide was placed at the 5' end of the ORF that encodes a light chain of an antibody against the thyroglobulin protein (cd5-1, SEQ ID NO: 123). The CD5 signal peptide sequence contains 7 potential initiation codons including 3 ATG, 1 TTG and 3 CTG codons. A series of expression constructs was generated. In one variation, ATG codons in the cd5 signal peptide were changed to ATC codons resulting in a Methionine to Isoleucine substitution (cd5-2, SEQ ID NO: 124). In another variation, CTG codons in the cd5 signal peptide were changed to CTC (cd5-3, SEQ ID NO: 125). In another variation, ATG codons were mutated to ATC codons resulting in a Methionine (M) to Isoleucine (I) amino acid substitution, and CTG codons were changed to CTCs (cd5-4, SEQ ID NO: 126). In another variation, ATG codons were changed to ATC codons resulting in a Methionine (M) to Isoleucine (I) amino acid substitution, CTG codons were changed to CTC codons, and the context of initiator AUG was improved by changing the codon 3' of it from CCC to GCT resulting in a Proline (P) to Arginine (R) amino acid substitution (cd5-5, SEQ ID NO: 127).

These constructs were then tested by transient transfection into Chinese Hamster Ovary (DG44) cells. In brief, 0.5 µg of each expression construct along with 2Ong of a co-transfection control plasmid that expresses the β-galactosidase reporter protein (pCMVβ, Clontech) was transfected into 100,000 DG44 cells using the Fugene 6 (Roche) transfection reagent according to the manufacturer's instructions. Twenty-four hours post transfection cells were lysed using 250 µl of lysis buffer. Lac Z reporter assay were performed to ensure equal transfection efficiencies between samples. 30 µl of supernatant was added to 10 µl of a 4×SDS gel loading buffer. The sample was heated at 72° C. for 10 minutes and loaded onto a 10% Bis-Tris/SDS polyacylamide gel. Proteins were transferred to a PVDF membrane and probed with an α-kappa light chain antibody.

Figure 4:
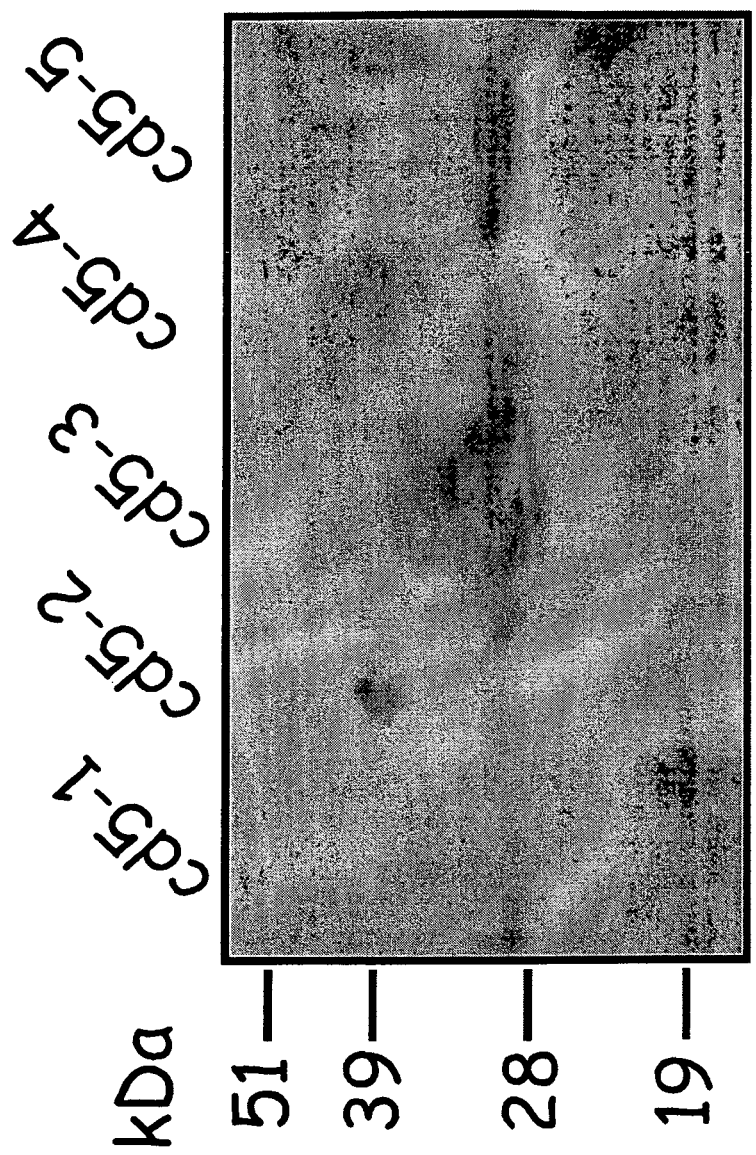
FIG. 4 shows a Western blot analysis of supernatants from DG44 cells transformed with the wild type CD5 (cd5-1) or modified CD5 signal peptide α-thyroglobulin light chain expression constructs (cd5-2 to cd5-5).

FIG. 4 shows a Western blot analysis of supernatant from DG44 cells transformed with the wild type (cd5-1) and modified cd5 signal peptide α-thyroglobulin light chain expression constructs (cd5-2 to cd5-5). Cell extracts were fractionated on 10% Bis-Tris gels in 1 x MOPS/SDS, transferred to PVDF membrane and probed with an α-kappa light chain antibody. Experiments were performed with supernatant from cells in which transfection efficiency was the same. The results show that the levels of the secreted antibody light chain product (above 28 kDa) in the supernatant of cells was substantially increased for the expression construct lacking CTG codons in the signal peptide (cd5-3). The expression construct lacking CTG, ATG codons and with improved nucleotide context around the authentic initiation codon in the signal peptide (fully rescued) also had levels of protein product in the supernatant that were substantially increased.

Thy-1 Variable Light chain ORF containing light chain signal peptide 1 (SEQ ID NO: 128) contains 104 potential initiation codons including 8 ATG, including the authentic initiation codon, 15 ATC, 6 ACG, 14 GTG, 4 TTG, 26 CTG, 16 AGG, 10 AAG, 3 ATA, and 2 ATT codons. Modifications were made in the signal peptide in which an AUG and CUG codons were removed (SEQ ID NO: 129). Thy-1 Variable Light chain ORF containing light chain signal peptide 2 (SEQ ID NOS: 130) contains 104 potential initiation codons including 7 ATG, including the authentic initiation codon, 16 ATC, 6 ACG, 13 GTG, 4 TTG, 27 CTG, 15 AGG, 10 AAG, 4 ATA, and 2 ATT codons. Thy-1 Variable Heavy chain ORF containing heavy chain signal peptide 1 contains 225 potential initiation codons including 18 ATG, including the authentic initiation codon, 14 ATC, 18 ACG, 42 GTG, 7 TTG, 43 CTG, 43 AGG, 33 AAG, 5 ATA, and 2 ATT codons (SEQ ID NO: 131). Modifications were made in the signal peptide by removing an AUG and CUG codon (SEQ ID NO: 132). Thy-1 Variable Heavy chain ORF containing heavy chain signal peptide 2 contains 227 potential initiation codons including 18 ATG, including the authentic initiation codon, 14 ATC, 18 ACG, 43 GTG, 9 TTG, 41 CTG, 43 AGG, 33 AAG, 5 ATA, and 3 ATT codons (SEQ ID NO: 133).

Thy-1 Variable Light chain ORF in which the signal peptide is replaced with the CD5 signal peptide (SEQ ID NO: 137) contains 104 potential initiation codons including 8 ATG, including the authentic initiation codon, 15 ATC, 6 ACG, 13 GTG, 5 TTG, 27 CTG, 14 AGG, 10 AAG, 3 ATA, and 2 ATT codons. A modification was made in which the ATG codons were changed to ATC codons that resulted in a Methionine (M) to Isoleucine (I) amino acid substitution (SEQ ID NO: 138). A modification was also made in which the CTG codons were changed to CTC codons (SEQ ID NO: 139). Another modification was made in which the ATG codons were mutated to ATC codons that resulted in Methionine (M) to Isoleucine (I) amino acid substitution and CTG codons were changed to CTC codons (SEQ ID NO: 140). Another modification was made in which ATG codons were changed to ATC codons resulting in a Methionine (M) to Isoleucine (I) amino acid substitution, CTG codons were changed to CTC codons, and the context of initiator AUG was improved by changing the codon 3' of it from CCC to GCT resulting in a Proline (P) to Arginine (R) amino acid substitution (SEQ ID NO: 141).

Signal peptides from other organisms were mutated as well (see Table 1). DNA sequences for signal peptides that function in yeast and mammalian cells were analyzed and mutated to create mutated versions (SEQ ID NOS: 145-156). It should be appreciated that in signal peptides, which are cleaved off of the protein, in-frame ATG codons can be mutated, e.g. to ATT or ATC, to encode Isoleucine, which is another hydrophobic amino acid. DNA constructs can be generated that contain these signal sequences fused in frame with a light chain from a human monoclonal antibody. Upon expression in different organisms (such as yeast Pichia pastoris and mammalian cell lines), protein gel and Western assay can be used to check the expression level of human light chain antibody.

TABLE 1

DNA sequences for signal peptide that function in yeast and mammalian cells.

| Organism/ signal sequence | DNA sequence | SEQ ID NO: |
|---|---|---|
| *Pichia pastoris*/ Kar2 Signal sequence | ATG/CTG/TCG/TTA/AAA/CCA/TCT/TGG/CTG/ ACT/TTG/GCG/GCA/TTA/ATG/TAT/GCC/ATG/ CTA/TTG/GTC/GTA/GTG/CCA/TTT/GCT/AAA/ CCT/GTT/AGA/GCT | 145 |
| *Pichia pastoris*/ Kar2 Signal sequence rescue version | ATG/CTC/TCG/TTA/AAA/CCA/TCT/TGG/CTC/ ACT/TTG/GCG/GCA/TTA/ATT/TAC/GCC/ATC/ CTA/TTG/GTC/GTA/GTG/CCA/TTT/GCT/AAA/ CCC/GTT/AGA/GCT | 146 |
| chicken/ lysozyme signal sequence | ATG/CTG/GGT/AAG/AAG/GAC/CCA/ATG/TGT/ CTT/GTT/TTG/GTC/TTG/TTG/GGA/TTG/ACT/ GCT/TTG/TTG/GGT/ATC/TGT/CAA/GGT | 147 |
| chicken/ lysozyme signal sequence rescue version | ATG/CTC/GGT/AAG/AAC/GAC/CCA/ATT/TGT/ CTT/GTT/TTG/GTC/TTG/TTG/GGA/TTG/ACC/ GCT/TTG/TTG/GGT/ATT/TGT/CAA/GGT | 148 |
| Human/ G-CSF-R signal sequence | ATG/AGG/CTG/GGA/AAC/TGC/AGC/CTG/ACT/ TGG/GCT/GCC/CTG/ATC/ATC/CTG/CTG/CTC/ CCC/GGA/AGT/CTG/GAG | 149 |
| Human/ G-CSF-R signal sequence rescue version | ATG/AGG/CTT/GGA/AAT/TGT/AGC/CTC/ACT/ TGG/GCC/GCC/CTC/ATC/ATC/CTC/CTT/CTC/ CCC/GGA/AGT/CTC/GAG | 150 |
| Human/ calcitonin receptor precursor signal sequence | ATG/AGG/ACA/TTT/ACA/AGC/CGG/TGC/TTG/ GCA/CTG/TTT/CTT/CTT/CTA/AAT/CAC/CCA/ ACC/CCA/ATT/CTT/CCT/G | 151 |
| Human/ calcitonin receptor precursor signal sequence rescue version | ATG/AGG/ACA/TTT/ACA/AGC/CGT/TGC/TTG/ GCA/CTC/TTT/CTT/CTT/CTA/AAT/CAC/CCA/ ACC/CCA/ATT/CTT/CCC/G | 152 |
| Human/ cell adhesion molecule 3 precursor (Immunoglobulin superfamily member, 4B) signal sequence | ATG/GCC/CCA/GCC/GCC/TCG/CTC/CTG/CTC/ CTG/CTC/CTG/CTG/TTC/GCC/TGC/TGC/TGG/ GCG/CCC/GGC/GGG/GCC | 153 |
| Human/ cell adhesion molecule 3 precursor (Immunoglobulin superfamily member, 4B) signal sequence rescue version | ATG/GCC/CCA/GCC/GCC/TCG/CTC/CTT/CTC/ CTT/CTC/CTT/CTC/TTT/GCT/TGT/TGT/TGG/ GCG/CCC/GGC/GGG/GCC | 154 |
| Human/ HLA class I histocompatibility antigen signal sequence | ATG/GTC/GCG/CCC/CGA/ACC/CTC/CTC/CTG/ CTA/CTC/TCG/GGG/GCC/CTG/GCC/CTG/ACC/ CAG/ACC/TGG/GCG | 155 |
| Human/ HLA class I histocompatibility antigen signal sequence rescue version | ATG/GTC/GCG/CCC/CGA/ACC/GTC/CTC/CTT/ CTT/CTC/TCG/GCG/GCC/CTC/GCC/CTT/ACC/ GAG/ACT/TGG/GCC | 156 |

HcRed 1

HcRed 1 encodes a far-red fluorescent protein whose excitation and emission maxima occur at 558 nm and 618 nm +/-4nm, respectively. HcRedl was generated by mutagenesis of a non-flourescent chromoptorein from the reef coral Heteractis crispa. The HcRed 1 coding sequence was subsequently human codon-optimized for higher expression in mammalian cells. This ORF contains 99 potential initiation codons including 9 ATG, including the authentic initiation codon, 8 ATC, 12 ACG, 16 GTG, 21 CTG, 18 AGG, and 15 AAG codons (SEQ ID NO: 134). Full and partial modifications of HcRedl ORF were generated (SEQ ID NOS: 135 and 136, respectively).

Erythropoietin (EPO)

Human erythropoietin (EPO) is a valuable therapeutic agent. Using methods described herein, the mRNA sequence that encodes for the human EPO this protein (provided below and available as GenBank Accession No. NM_000799) is optimized to eliminate multiple translation initiation sites within this mRNA transcript.

An exemplary human erythropoietin (EPO) protein is encoded by the following mRNA transcript, wherein the sequence encoding the mature peptide is underlined, all potential translation initiation start sites within all three reading frames are bolded, the canonical initiator codon corresponding to methionine is capitalized, and uracil (u) is substituted for thymidine (t) (SEQ ID NO: 111):

larly hydrophobic, non-polar, and occupy equivalent Van der Waals volumes. Thus, a substitution of leucine or isoleucine for methionine would not affect protein folding. Leucine is a preferred amino acid for methionine substitution. Alternatively, the amino acids tyrosine or phenylalanine can be sub-

```
   1 cccggagccggaccggggccaccgcgcccgctctgctccgacaccgcgcccctggacag
  61 ccgccctctcctccaggcccgtggggctggccctgcaccgccgagcttcccgggATGagg
 121 gccccggtgtggtcacccggcgcgcccaggtcgctgagggaccccggccaggcgcgga
 181 gATGggggtgcacgaATGtcctgcctggctgtggcttctcctgtccctgctgtcgctccc
 241 tctgggcctcccagtcctgggcgccccaccacgcctcatctgtgacagccgagtcctgca
 301 gaggtacctcttggaggccaaggaggccgagaatatcacgacgggctgtgctgaacactg
 361 cagcttgaATGagaatatcactgtcccagacaccaaagttaatttctATGcctggaagag
 421 gATGgaggtcgggcagcaggccgtagaagtctggcagggcctggccctgctgtcggaagc
 481 tgtcctgcggggccaggccctgttggtcaactcttcccagccgtgggagccctgcagct
 541 gcATGtgcataaagccgtcagtggccttcgcagcctcaccactctgcttcgggctctggg
 601 agcccagaaggaagccatctcccctccagATGcggcctcagctgctccactccgaacaat
 661 cactgctgacactttccgcaaactcttccgagtctactccaatttcctccgggaaagct
 721 gaagctgtacacaggggaggcctgcaggacaggggacagATGaccaggtgtgtccacctg
 781 ggcatatccaccacctccctcaccaacattgcttgtgccacaccctccccgccactcct
 841 gaaccccgtcgagggctctcagctcagcgccagcctgtcccATGgacactccagtgcca
 901 gcaATGacatctcaggggccagaggaactgtccagagagcaactctgagatctaaggATG
 961 tcacagggccaacttgagggcccagagcaggaagcattcagagagcagctttaaactcag
1021 ggacagagccATGctgggaagacgcctgagctcactcggcaccctgcaaaatttgATGcc
1081 aggacacgctttggaggcgatttacctgttttcgcacctaccatcagggacaggATGacc
1141 tggagaacttaggtggcaagctgtgacttctccaggtctcacgggcATGggcactccctt
1201 ggtggcaagagcccccttgacaccggggtggtgggaaccATGaagacaggATGggggctg
1261 gcctctggctctcATGgggtccaagtttgtgtattcttcaacctcattgacaagaactg
1321 aaaccaccaaaaaaaaaaaa
```

To preserve the resultant amino acid sequence, silent or conserved substitutions are made wherever possible. In the case of Methionine and tryptophan, which are only encoded only by one codon (aug/atg) and (ugg/tgg), respectively, a substitution replaces the sequence encoding methionine or tryptophan with a sequence encoding an amino acid of similar physical properties. Physical properties that are considered important when making conservative amino acid substitutions include, but are not limited to, side chain geometry, size, and branching; hydrophobicity; polarity; acidity; aromatic versus aliphatic structure; and Van der Waals volume. For instance, the amino acids leucine or isoleucine can be substituted for methionine because these amino acids are all simistituted for tryptophan because these amino acids are all similarly aromatic, and occupy quivalent Van der Waals volumes.

The following sequence is an example of a modified mRNA transcript encoding human erythropoietin (EPO), wherein all potential translation initiation start sites upstream of the demonstrated initiator methionine (encoded by nucleotides182-184) and those potential translation initiation start sites downstream of the demonstrated initiator methionine within the coding region, are mutated (mutations in italics) (SEQ ID NO: 113).

```
  1 cccggagccggaccggggccaccgcgcccgctctactccgacaccgcgcccctagacag
 61 ccgccctctcctccaggcccgtagggctagccctacaccgccgagcttcccgggTTAagg
121 gccccggtctagtcacccggcgcgcccaggtcgctaagggaccccggccaggcgcgga
```

-continued

```
 181 gATGggggtacacaaTTAtcctacctagctctagcttctcctatccctactatcgctccc 241 tctaggcctcccagtcctaggcgccccaccacacctcctctttaacagccgagtcctaga 301 gaggtacctcttagaggccaaggaggccgagaatatcacgacgggctgtgctgaacactg 361 cagcttgaTTAagattttaactatcccagacaccaaagttattatctTTAcctagaagag 421 gTTAgaggtcgggcagcaggccgtagaagtctagcagggcctagccctactatcggaagc 481 tgtcctacggggccaggccctattagtcaactcttcccagccgtaggagcccctacagct 541 gcCTCtagttaaagccgtcagtagccttcgcagcctcaccactctacttcgggctctagg 601 agcccagaaggaagccctctccctccagTTAcggcctcagctactccactccgaacaat 661 cactactaacactttccgcaaactcttccgagtctactccaatatcctccggggaaagct 721 gaagctatacacaggggaggcctacaggacaggggacagTTAaccagttttatccaccta 781 ggcttttacaccacctccctcaccaacttaccttttaccacaccctccccgccactcct 841 gaaccccgtcgaggggctctcagctcagcgccagcctatcccTTAgacactccagtacca 901 gcaTTAacttatcaggggccagaggaactatccagagagcaactctaagttataaggTTA 961 tcacagggccaacttaagggcccagagcaggaagcttacagagagcagctttaaactcag 1021 ggacagagccTTActaggaagacacctaagctcactcggcaccctacaaattttaTTAcc 1081 aggacacactttagaggcgttatacctattttcgcacctaccttaagggacaggTTAacc 1141 tggagaacttaggtagcaagctctcacttctccaggtctcacaggcTTAggcactcccctt 1201 ggtagcaagagccccctaacaccggggtagtaggaaccTTAaagacaggTTAggggcta 1261 gcctctagctctcTTAgggtccaagttcttattacttcaacctcttacacaagaacta 1321 aaaccaccaaaaaaaaaaaa
```

The unmodified open reading frame for erythropoietin contains 88 potential initiation codons (8 ATG, including the authentic initiation codon, 5 ATC, 4 ACG, 7 GTG, 3 TTG, 32 CTG, 14 AGG, 10 AAG, 3 ATA, and 2 ATT codons) (SEQ ID NO: 112). Modifications were made including a modified signal peptide by removal of most of the potential initiation codons (SEQ ID NO: 116), removal of ATG and CTGs of the signal peptide (SEQ ID NO: 211), removal of ATG, CTG and ACG codons resulting in a Glutamic acid (E) to Glutamine (Q) amino acid substitution (SEQ ID NO: 118) or a Histidine (H) to Argenine (R) amino acid substitution (SEQ ID NO: 119).

Example 2

Modification of miRNA Binding Sites within mRNA Transcripts

MicroRNA (miRNA) binding to target mRNA transcripts decreases translation efficiency by either inducing degradation of the target mRNA transcript, or by preventing translation of the target mRNA transcript. To improve translation efficiency of mRNA transcripts encoding commercially-valuable human proteins, all known or predicted miRNA binding sites within a target mRNA's 5' leader sequence, 5' untranslated region (UTR) sequence, coding sequence, and 3' untranslated region (UTR) sequence are first identified, and secondly mutated or altered in order to inhibit miRNA binding.

In a preferred aspect of this method, the seed sequence, comprising the first eight 5'- nucleotides of the mature miRNA sequence is specifically targeted. Seed sequences either include 5' nucleotides 1-7 or 2-8 of the mature miRNA sequence. Thus, a seed sequence, for the purposes of this method, encompasses both alternatives. The miRNA seed sequence is functionally significant because it is the only portion of the miRNA which binds according to Watson-Crick base-pairing rules. Without absolute complementarity of binding within the seed sequence region of the miRNA, binding of the miRNA to its target mRNA does not occur. However, unlike most nucleotide pairings, the seed sequence of a miRNA is capable of pairing with a target mRNA such that a guanine nucleotide pairs with a uracil nucleotide, known as the G:U wobble.

For example, human erythropoietin (EPO) is a valuable therapeutic agent that has been difficult to produce in sufficient quantities. Using the instant methods, the sequence of the mRNA sequence that encodes this protein (GenBank Accession No. NM_000799) is optimized to inhibit miRNA down-regulation. The PicTar Web Interface (publicly available at pictar.mdc_berlin.de/cgi-bin/PicTar_vertebrate.cgi) predicted that human miRNAs hsa-miR-328 and hsa-miR-122a targeted the mRNA encoding for human EPO (the mature and seed sequences of these miRNAs are provided below in Table 2). Thus, in the case of hsa-miR-122a, for instance, having a seed sequence of uggagugu, one or more nucleotides are mutated such that hsa-miR-122a no longer binds, and the seed sequence of another known miRNA is not created. One possible mutated hsa-miR-122a seed sequence that should prevent binding is "uagagugu." It is unlikely that this mutated seed sequence belongs to another known mRNA because this sequence is not represented, for instance, within Table 2 below.

Similarly, the PicTar Web Interface predicted that human miRNAs hsa-miR-149, hsa-let7f, hsa-let7c, hsa-let7b, hsa-let7g, hsa-let7a, hsa-miR-98, hsa-let7i, hsa-let7e and hsa-miR-26b targeted the mRNA encoding for human interferon beta 2 (also known as IL-6, Genbank Accession No. NM_000600) (the mature and seed sequences of these miRNAs are provided below in Table 2).

MiRNA binding sites can also be identified by entering any sequence of less than 1000 base pairs into the Sanger Institute's MiRNA:Sequence database (publicly available at microrna.sanger.ac.uk/sequences/search.shtml).

TABLE 2

Known Human MiRNAs, mature sequences, and seed sequences.

| MiRNA | Mature Sequence | SEQ ID NO: | Seed Sequence |
|---|---|---|---|
| hsa-let-7a | ugagguaguagguuguauaguu | 1 | ugagguag |
| hsa-let-7b | ugagguaguagguugugugguu | 2 | ugagguag |
| hsa-let-7c | ugagguaguagguuguaugguu | 3 | ugagguag |
| hsa-let-7d | agagguaguagguugcauaguu | 4 | agagguag |
| hsa-let-7e | ugagguaggagguuguauaguu | 5 | ugagguag |
| hsa-let-7f | ugagguaguagauuguauaguu | 6 | ugagguag |
| hsa-let-7g | ugagguaguaguuuguacaguu | 7 | ugagguag |
| hsa-let-7i | ugagguaguaguuugugcuguu | 8 | ugagguag |
| hsa-miR-1 | uggaauguaaagaaguauguau | 9 | uggaaugu |
| hsa-miR-100 | aacccguagauccgaacuugug | 10 | aacccgua |
| hsa-miR-101 | uacaguacugugauaacugaa | 11 | uacaguac |
| hsa-miR-103 | agcagcauuguacagggcuauga | 12 | agcagcau |
| hsa-miR-105 | ucaaaugcucagacuccuguggu | 13 | ucaaaugc |
| hsa-miR-106a | aaaagugcuuacagugcagguag | 14 | aaaagugc |
| hsa-miR-106b | uaaagugcugacagugcagau | 15 | uaaagugc |
| hsa-miR-107 | agcagcauuguacagggcuauca | 16 | agcagcau |
| hsa-miR-10a (mmu-miR-184) | uggacggagaacugauaagggu | 17 | uggacgga |
| hsa-miR-10b | uacccuguagaaccgaauuugug | 18 | uacccugu |
| hsa-miR-122a | uggagugugacaaugguguuug | 19 | uggagugu |
| hsa-miR-124a | uaaggcacgcggugaaugcc | 20 | uaaggcac |
| hsa-miR-125a | ucccugagacccuuuaaccuguga | 21 | ucccugag |
| hsa-miR-125b | ucccugagacccuaacuuguga | 22 | ucccugag |
| hsa-miR-126 | Ucguaccgugaguaauaaugcg | 23 | ucguaccg |
| hsa-miR-127 | cugaagcucagagggcucugau | 24 | cugaagcu |

TABLE 2-continued

Known Human MiRNAs, mature sequences, and seed sequences.

| MiRNA | Mature Sequence | SEQ ID NO: | Seed Sequence |
|---|---|---|---|
| hsa-miR-128 | ucacagugaaccggucucuuu | 25 | ucacagug |
| hsa-miR-129 | cuuuuugcggucugggcuugc | 26 | cuuuuugc |
| hsa-miR-130a | cagugcaauguuaaaagggcau | 27 | cagugcaa |
| hsa-miR-130b | cagugcaaugaugaaagggcau | 28 | cagugcaa |
| hsa-miR-132 | uaacagucuacagccauggucg | 29 | uaacaguc |
| hsa-miR-133a | uuugguccccuucaaccagcug | 30 | uuuggucc |
| hsa-miR-133b | uuugguccccuucaaccagcua | 31 | uuuggucc |
| hsa-miR-134 | ugugacugguugaccagagggg | 32 | ugugacug |
| hsa-miR-135a | uauggcuuuuuauuccuauguga | 33 | uauggcuu |
| hsa-miR-135b | uauggcuuuucauuccuauguga | 34 | uauggcuu |
| hsa-miR-136 | acuccauuuguuuugaugaugga | 35 | acuccauu |
| hsa-miR-137 | uuauugcuuaagaauacgcguag | 36 | uuauugcu |
| hsa-miR-138 | agcugguguugugaaucaggccg | 37 | agcuggug |
| hsa-miR-139 | ucuacagugcacgugucuccag | 38 | ucuacagu |
| hsa-miR-140 | cagugguuuuacccuaugguag | 39 | cagugguu |
| hsa-miR-141 | uaacacugucugguaaagaugg | 40 | uaacacug |
| hsa-miR-142-5p | cauaaaguagaaagcacuacu | 41 | cauaaagu |
| hsa-miR-143 | ugagaugaagcacuguagcuc | 42 | ugagauga |
| hsa-miR-144 | uacaguauagaugauguacu | 43 | uacaguau |
| hsa-miR-145 | guccaguuuucccaggaaucccu | 44 | guccaguu |
| hsa-miR-146 | ugagaacugaauuccaugggu u | 45 | ugagaacu |
| hsa-miR-147 | guguguggaaaugcuucugc | 46 | gugugugg |
| hsa-miR-148a | ucagugcacuacagaacuuugu | 47 | ucagugca |
| hsa-miR-148b | ucagugcaucacagaacuuugu | 48 | ucagugca |
| hsa-miR-149 | ucuggcuccgugucuucacuccc | 49 | ucuggcuc |
| hsa-miR-150 | ucucccaacccuuguaccagug | 50 | ucucccaa |
| hsa-miR-151 | ucgaggagcucacagucuagu | 51 | ucgaggag |
| hsa-miR-152 | ucagugcaugacagaacuugg | 52 | ucagugca |
| hsa-miR-153 | uugcauagucacaaaagugauc | 53 | uugcauag |
| hsa-miR-154 | uagguuauccguguugccuucg | 54 | uagguuau |
| hsa-miR-155 | uuaaugcuaaucgugauaggggu | 55 | uuaaugcu |
| hsa-miR-15a | uagcagcacauaaugguuugug | 56 | uagcagca |
| hsa-miR-15b | uagcagcacaucaugguuuaca | 57 | uagcagca |
| hsa-miR-16 | uagcagcacguaaauauuggcg | 58 | uagcagca |
| hsa-miR-17 | caaagugcuuacagugcagguag | 60 | caaagugc |
| hsa-miR-18 | uaaggugcaucuagugcagauag | 61 | uaaggugc |

TABLE 2-continued

Known Human MiRNAs, mature sequences, and seed sequences.

| MiRNA | Mature Sequence | SEQ ID NO: | Seed Sequence |
|---|---|---|---|
| hsa-miR-181a | aacauucaacgcugucggugagu | 62 | aacauuca |
| hsa-miR-181b | Aacauucauugcugucggugggu | 63 | aacauuca |
| hsa-miR-181c | aaccaucgaccguugaguggac | 64 | aaccaucg |
| hsa-miR-182 | uuuggcaaugguagaacucacacu | 65 | uuuggcaa |
| hsa-miR-183 | uauggcacugguagaauucacu | 66 | uauggcac |
| hsa-miR-184 | uggacgagaacugauaagggu | 67 | uggacgga |
| hsa-miR-185 | uggagagaaaggcaguuccuga | 68 | uggagaga |
| hsa-miR-186 | caaagaauucuccuuuugggcu | 69 | caaagaau |
| hsa-miR-187 | ucgugucuuguguugcagccgg | 70 | ucgugucu |
| hsa-miR-188 | caucccuugcaugguggaggg | 71 | caucccuu |
| hsa-miR-190 | ugauauguuugauauauuaggu | 72 | ugauaugu |
| hsa-miR-191 | caacggaaucccaaaagcagcug | 73 | caacggaa |
| hsa-miR-192 | cugaccuaugaauugacagcc | 74 | cugaccua |
| hsa-miR-193 | ugggucuuugcgggcgagauga | 75 | ugggucuu |
| hsa-miR-194 | uguaacagcaacuccaugugga | 76 | uguaacag |
| hsa-miR-195 | uagcagcacagaaauauuggc | 77 | uagcagca |
| hsa-miR-196a | uagguaguuucauguuguuggg | 78 | uagguagu |
| hsa-miR-196b | uagguaguuuccuguuguuggg | 79 | uagguagu |
| hsa-miR-197 | uucaccaccuucuccacccagc | 80 | uucaccac |
| hsa-miR-198 | gguccagaggggagauagguuc | 81 | gguccaga |
| hsa-miR-199a | cccaguguucagacuaccuguuc | 82 | cccagugu |
| hsa-miR-199b | cccaguguuuagacuaucuguuc | 83 | cccagugu |
| hsa-miR-19a | aguuuugcauaguugcacuaca | 84 | aguuuugc |
| hsa-miR-19b | ugugcaaauccaugcaaaacuga | 85 | ugugcaaa |
| hsa-miR-20 | uaaagcuuuauagugcagguag | 86 | uaaagugc |
| hsa-miR-200a | uaacacugucugguaacgaugu | 87 | uaacacug |
| hsa-miR-200b | uaauacugccugguaaugauga | 88 | uaauacug |
| hsa-miR-200c | uaauacugccggguaaugaugga | 89 | uaauacug |
| hsa-miR-203 | gugaaauguuuaggaccacuag | 90 | gugaaaug |
| hsa-miR-204 | uucccuuugucauccuaugccu | 91 | uucccuuu |
| hsa-miR-205 | uccuucauccaccggagucug | 92 | uccuucau |
| hsa-miR-206 | uggaauguaaggaagugugugg | 93 | uggaaugu |
| hsa-miR-208 | auaagacgagcaaaaagcuugu | 94 | auaagacg |
| hsa-miR-21 | uagcuuaucagacugauguuga | 95 | uagcuuau |
| hsa-miR-210 | cugugcgugugacagcggcuga | 96 | cugugcgu |
| hsa-miR-211 | uucccuuugucauccuucgccu | 97 | uucccuuu |
| hsa-miR-212 | uaacagucuccagucacgcc | 98 | uaacaguc |
| hsa-miR-213 | aacauucaacgcugucggugagu | 61 | aacauuca |
| (hsa-miR-181a) | | | |
| hsa-miR-214 | acagcaggcacagacaggcagu | 99 | acagcagg |
| hsa-miR-215 | augaccuaugaauugacagac | 100 | augaccua |
| hsa-miR-216 | uaaucucagcuggcaacuguga | 101 | uaaucuca |
| hsa-miR-217 | uacugcaucaggaacugauugga | 102 | uacugcau |
| hsa-miR-218 | uugugcuugaucuaaccaugu | 103 | uugugcuu |
| hsa-miR-219 | ugauugccaaacgcaauucu | 104 | ugauuguc |
| hsa-miR-22 | aagcugccaguugaagaacugu | 105 | aagcugcc |
| hsa-miR-220 | ccacaccguaucgacacuuu | 106 | ccacaccg |
| hsa-miR-221 | agcuacauugucugcuggguuuc | 107 | agcuacau |
| hsa-miR-222 | agcuacaucuggcuacugggu | 108 | agcuacau |
| hsa-miR-223 | ugucaguuugucaaauacccca | 109 | ugucaguu |
| hsa-miR-224 | caagucacuaguguuccguu | 110 | caagucac |
| hsa-miR-26b | uucaaguaauucaggauaggu | 114 | uucaagua |

The miR-183 binding sequence (SEQ ID NO: 59) was mutated (SEQ ID NO: 142) and embedded into the coding sequence of a reporter gene, such as in a CAT gene that also contains a FLAG Tag (SEQ ID NO: 143). This allows for the evaluation of expression in cells by Western blot analyses using an anti-FLAG Tag antibody in which mutations of the miR-183 binding sequence were made (SEQ ID NO: 144).

What is claimed is:

1. A method of improving full-length protein expression efficiency comprising:
   a) providing a polynucleotide comprising:
      i) a coding sequence for the full-length protein;
      ii) a primary initiation codon that is upstream of the coding sequence of the full-length protein, said primary initiation codon encoding the first amino acid of the coding sequence of the full-length protein; and
      iii) one or more secondary initiation codons located within the coding sequence of the full-length protein downstream of the primary initiation codon; and
   b) mutating the one or more secondary initiation codons located within the coding sequence of the full-length protein downstream of the primary initiation codon, wherein the mutation results in a decrease in initiation of protein synthesis at the one or more secondary initiation codons, thereby increasing expression efficiency of the full-length protein initiated at the primary initiation codon, wherein mutating the one or more secondary initiation codons located within the coding sequence of the full-length protein downstream of the primary initiation codon comprises mutating one or more nucleotides such that the amino acid sequence of the protein remains unaltered.

* * * * *

SEQUENCE LISTING

<160> NUMBER OF SEQ ID NOS: 156

<210> SEQ ID NO 1
<211> LENGTH: 22
<212> TYPE: RNA
<213> ORGANISM: human

<400> SEQUENCE: 1
ugagguagua gguuguauag uu                        22

```
<210> SEQ ID NO 2
<211> LENGTH: 22
<212> TYPE: RNA
<213> ORGANISM: human

<400> SEQUENCE: 2
ugagguagua gguugugugg uu                                              22

<210> SEQ ID NO 3
<211> LENGTH: 22
<212> TYPE: RNA
<213> ORGANISM: human

<400> SEQUENCE: 3
ugagguagua gguuguaugg uu                                              22

<210> SEQ ID NO 4
<211> LENGTH: 22
<212> TYPE: RNA
<213> ORGANISM: human

<400> SEQUENCE: 4
agagguagua gguugcauag uu                                              22

<210> SEQ ID NO 5
<211> LENGTH: 22
<212> TYPE: RNA
<213> ORGANISM: human

<400> SEQUENCE: 5
ugagguagga gguuguauag uu                                              22

<210> SEQ ID NO 6
<211> LENGTH: 22
<212> TYPE: RNA
<213> ORGANISM: human

<400> SEQUENCE: 6
ugagguagua gauuguauag uu                                              22

<210> SEQ ID NO 7
<211> LENGTH: 22
<212> TYPE: RNA
<213> ORGANISM: human

<400> SEQUENCE: 7
ugagguagua guuuguacag uu                                              22

<210> SEQ ID NO 8
<211> LENGTH: 22
<212> TYPE: RNA
<213> ORGANISM: human

<400> SEQUENCE: 8
ugagguagua guuugugcug uu                                              22

<210> SEQ ID NO 9
<211> LENGTH: 22
<212> TYPE: RNA
<213> ORGANISM: human

<400> SEQUENCE: 9
```

-continued uggaauguaa agaaguaugu au                                    22

<210> SEQ ID NO 10
<211> LENGTH: 22
<212> TYPE: RNA
<213> ORGANISM: human

<400> SEQUENCE: 10
aacccguaga uccgaacuug ug                                    22

<210> SEQ ID NO 11
<211> LENGTH: 21
<212> TYPE: RNA
<213> ORGANISM: human

<400> SEQUENCE: 11
uacaguacug ugauaacuga a                                     21

<210> SEQ ID NO 12
<211> LENGTH: 23
<212> TYPE: RNA
<213> ORGANISM: human

<400> SEQUENCE: 12
agcagcauug uacagggcua uga                                   23

<210> SEQ ID NO 13
<211> LENGTH: 23
<212> TYPE: RNA
<213> ORGANISM: human

<400> SEQUENCE: 13
ucaaaugcuc agacuccugu ggu                                   23

<210> SEQ ID NO 14
<211> LENGTH: 23
<212> TYPE: RNA
<213> ORGANISM: human

<400> SEQUENCE: 14
aaaagugcuu acagugcagg uag                                   23

<210> SEQ ID NO 15
<211> LENGTH: 21
<212> TYPE: RNA
<213> ORGANISM: human

<400> SEQUENCE: 15
uaaagugcug acagugcaga u                                     21

<210> SEQ ID NO 16
<211> LENGTH: 23
<212> TYPE: RNA
<213> ORGANISM: human

<400> SEQUENCE: 16
agcagcauug uacagggcua uca                                   23

<210> SEQ ID NO 17
<211> LENGTH: 22
<212> TYPE: RNA
<213> ORGANISM: human

<400> SEQUENCE: 17
uggacggaga acugauaagg gu                                                22

<210> SEQ ID NO 18
<211> LENGTH: 23
<212> TYPE: RNA
<213> ORGANISM: human

<400> SEQUENCE: 18
uacccuguag aaccgaauuu gug                                               23

<210> SEQ ID NO 19
<211> LENGTH: 22
<212> TYPE: RNA
<213> ORGANISM: human

<400> SEQUENCE: 19
uggaguguga caauggnguu ug                                                22

<210> SEQ ID NO 20
<211> LENGTH: 20
<212> TYPE: RNA
<213> ORGANISM: human

<400> SEQUENCE: 20
uaaggcacgc ggugaaugcc                                                   20

<210> SEQ ID NO 21
<211> LENGTH: 24
<212> TYPE: RNA
<213> ORGANISM: human

<400> SEQUENCE: 21
ucccugagac ccuuuaaccu guga                                              24

<210> SEQ ID NO 22
<211> LENGTH: 22
<212> TYPE: RNA
<213> ORGANISM: human

<400> SEQUENCE: 22
ucccugagac ccuaacuugu ga                                                22

<210> SEQ ID NO 23
<211> LENGTH: 22
<212> TYPE: RNA
<213> ORGANISM: human

<400> SEQUENCE: 23
ucguaccgug aguaauaaug cg                                                22

<210> SEQ ID NO 24
<211> LENGTH: 22
<212> TYPE: RNA
<213> ORGANISM: human

<400> SEQUENCE: 24
cugaagcuca gagggcucug au                                                22

<210> SEQ ID NO 25
<211> LENGTH: 21
<212> TYPE: RNA
<213> ORGANISM: human

```
<400> SEQUENCE: 25
ucacagugaa ccggucucuu u                                              21

<210> SEQ ID NO 26
<211> LENGTH: 21
<212> TYPE: RNA
<213> ORGANISM: human

<400> SEQUENCE: 26
cuuuuugcgg ucugggcuug c                                              21

<210> SEQ ID NO 27
<211> LENGTH: 22
<212> TYPE: RNA
<213> ORGANISM: human

<400> SEQUENCE: 27
cagugcaaug uuaaaagggc au                                             22

<210> SEQ ID NO 28
<211> LENGTH: 22
<212> TYPE: RNA
<213> ORGANISM: human

<400> SEQUENCE: 28
cagugcaaug augaaagggc au                                             22

<210> SEQ ID NO 29
<211> LENGTH: 22
<212> TYPE: RNA
<213> ORGANISM: human

<400> SEQUENCE: 29
uaacagucua cagccauggu cg                                             22

<210> SEQ ID NO 30
<211> LENGTH: 22
<212> TYPE: RNA
<213> ORGANISM: human

<400> SEQUENCE: 30 uuugguccccc uucaaccagc ug                                            22

<210> SEQ ID NO 31
<211> LENGTH: 22
<212> TYPE: RNA
<213> ORGANISM: human

<400> SEQUENCE: 31 uuugguccccc uucaaccagc ua                                            22

<210> SEQ ID NO 32
<211> LENGTH: 22
<212> TYPE: RNA
<213> ORGANISM: human

<400> SEQUENCE: 32
ugugacuggu ugaccagagg gg                                             22

<210> SEQ ID NO 33
<211> LENGTH: 23
<212> TYPE: RNA
<213> ORGANISM: human
```

```
<400> SEQUENCE: 33
uauggcuuuu uauuccuaug uga                                              23

<210> SEQ ID NO 34
<211> LENGTH: 23
<212> TYPE: RNA
<213> ORGANISM: human

<400> SEQUENCE: 34
uauggcuuuu cauuccuaug uga                                              23

<210> SEQ ID NO 35
<211> LENGTH: 23
<212> TYPE: RNA
<213> ORGANISM: human

<400> SEQUENCE: 35
acuccauuug uuugaugau gga                                               23

<210> SEQ ID NO 36
<211> LENGTH: 23
<212> TYPE: RNA
<213> ORGANISM: human

<400> SEQUENCE: 36
uuauugcuua agaauacgcg uag                                              23

<210> SEQ ID NO 37
<211> LENGTH: 23
<212> TYPE: RNA
<213> ORGANISM: human

<400> SEQUENCE: 37
agcugguguu gugaaucagg ccg                                              23

<210> SEQ ID NO 38
<211> LENGTH: 22
<212> TYPE: RNA
<213> ORGANISM: human

<400> SEQUENCE: 38
ucuacagugc acgucucc ag                                                 22

<210> SEQ ID NO 39
<211> LENGTH: 22
<212> TYPE: RNA
<213> ORGANISM: human

<400> SEQUENCE: 39
cagugguuuu acccuauggu ag                                               22

<210> SEQ ID NO 40
<211> LENGTH: 22
<212> TYPE: RNA
<213> ORGANISM: human

<400> SEQUENCE: 40
uaacacuguc ugguaaagau gg                                               22

<210> SEQ ID NO 41
<211> LENGTH: 21
<212> TYPE: RNA
```

```
<213> ORGANISM: Human

<400> SEQUENCE: 41
cauaaaguag aaagcacuac u                                            21

<210> SEQ ID NO 42
<211> LENGTH: 21
<212> TYPE: RNA
<213> ORGANISM: human

<400> SEQUENCE: 42
ugagaugaag cacuguagcu c                                            21

<210> SEQ ID NO 43
<211> LENGTH: 20
<212> TYPE: RNA
<213> ORGANISM: human

<400> SEQUENCE: 43
uacaguauag augauguacu                                              20

<210> SEQ ID NO 44
<211> LENGTH: 23
<212> TYPE: RNA
<213> ORGANISM: human

<400> SEQUENCE: 44
guccaguuuu cccaggaauc ccu                                          23

<210> SEQ ID NO 45
<211> LENGTH: 22
<212> TYPE: RNA
<213> ORGANISM: human

<400> SEQUENCE: 45
ugagaacuga auuccauggg uu                                           22

<210> SEQ ID NO 46
<211> LENGTH: 20
<212> TYPE: RNA
<213> ORGANISM: human

<400> SEQUENCE: 46
guguguggaa augcuucugc                                              20

<210> SEQ ID NO 47
<211> LENGTH: 22
<212> TYPE: RNA
<213> ORGANISM: human

<400> SEQUENCE: 47
ucagugcacu acagaacuuu gu                                           22

<210> SEQ ID NO 48
<211> LENGTH: 22
<212> TYPE: RNA
<213> ORGANISM: human

<400> SEQUENCE: 48
ucagugcauc acagaacuuu gu                                           22

<210> SEQ ID NO 49
<211> LENGTH: 23
```

```
<212> TYPE: RNA
<213> ORGANISM: human

<400> SEQUENCE: 49
ucuggcuccg ugucuucacu ccc                                    23

<210> SEQ ID NO 50
<211> LENGTH: 22
<212> TYPE: RNA
<213> ORGANISM: human

<400> SEQUENCE: 50
ucucccaacc cuuguaccag ug                                     22

<210> SEQ ID NO 51
<211> LENGTH: 21
<212> TYPE: RNA
<213> ORGANISM: human

<400> SEQUENCE: 51
ucgaggagcu cacagucuag u                                      21

<210> SEQ ID NO 52
<211> LENGTH: 21
<212> TYPE: RNA
<213> ORGANISM: human

<400> SEQUENCE: 52
ucagugcaug acagaacuug g                                      21

<210> SEQ ID NO 53
<211> LENGTH: 22
<212> TYPE: RNA
<213> ORGANISM: human

<400> SEQUENCE: 53
uugcauaguc acaaaaguga uc                                     22

<210> SEQ ID NO 54
<211> LENGTH: 22
<212> TYPE: RNA
<213> ORGANISM: human

<400> SEQUENCE: 54
uagguuaucc guguugccuu cg                                     22

<210> SEQ ID NO 55
<211> LENGTH: 23
<212> TYPE: RNA
<213> ORGANISM: human

<400> SEQUENCE: 55
uuaaugcuaa ucgugauagg ggu                                    23

<210> SEQ ID NO 56
<211> LENGTH: 22
<212> TYPE: RNA
<213> ORGANISM: human

<400> SEQUENCE: 56
uagcagcaca uaaugguuug ug                                     22

<210> SEQ ID NO 57
```

```
<211> LENGTH: 22
<212> TYPE: RNA
<213> ORGANISM: human

<400> SEQUENCE: 57
uagcagcaca ucaugguuua ca                                              22

<210> SEQ ID NO 58
<211> LENGTH: 22
<212> TYPE: RNA
<213> ORGANISM: human

<400> SEQUENCE: 58
uagcagcacg uaaauauugg cg                                              22

<210> SEQ ID NO 59
<211> LENGTH: 24
<212> TYPE: RNA
<213> ORGANISM: human

<400> SEQUENCE: 59
aaagcgaauu cucacaggcc auca                                            24

<210> SEQ ID NO 60
<211> LENGTH: 23
<212> TYPE: RNA
<213> ORGANISM: human

<400> SEQUENCE: 60
caaagugcuu acagugcagg uag                                             23

<210> SEQ ID NO 61
<211> LENGTH: 23
<212> TYPE: RNA
<213> ORGANISM: human

<400> SEQUENCE: 61
uaaggugcau cuagugcaga uag                                             23

<210> SEQ ID NO 62
<211> LENGTH: 23
<212> TYPE: RNA
<213> ORGANISM: human

<400> SEQUENCE: 62
aacauucaac gcugucggug agu                                             23

<210> SEQ ID NO 63
<211> LENGTH: 23
<212> TYPE: RNA
<213> ORGANISM: human

<400> SEQUENCE: 63
aacauucauu gcugucggug ggu                                             23

<210> SEQ ID NO 64
<211> LENGTH: 22
<212> TYPE: RNA
<213> ORGANISM: human

<400> SEQUENCE: 64
aaccaucgac cguugagugg ac                                              22
```

```
<210> SEQ ID NO 65
<211> LENGTH: 24
<212> TYPE: RNA
<213> ORGANISM: human

<400> SEQUENCE: 65
uuuggcaaug guagaacuca cacu                                              24

<210> SEQ ID NO 66
<211> LENGTH: 22
<212> TYPE: RNA
<213> ORGANISM: human

<400> SEQUENCE: 66
uauggcacug guagaauuca cu                                                22

<210> SEQ ID NO 67
<211> LENGTH: 22
<212> TYPE: RNA
<213> ORGANISM: human

<400> SEQUENCE: 67
uggacggaga acugauaagg gu                                                22

<210> SEQ ID NO 68
<211> LENGTH: 22
<212> TYPE: RNA
<213> ORGANISM: human

<400> SEQUENCE: 68
uggagagaaa ggcaguuccu ga                                                22

<210> SEQ ID NO 69
<211> LENGTH: 22
<212> TYPE: RNA
<213> ORGANISM: human

<400> SEQUENCE: 69
caaagaauuc uccuuuuggg cu                                                22

<210> SEQ ID NO 70
<211> LENGTH: 22
<212> TYPE: RNA
<213> ORGANISM: human

<400> SEQUENCE: 70
ucgugucuug uguugcagcc gg                                                22

<210> SEQ ID NO 71
<211> LENGTH: 21
<212> TYPE: RNA
<213> ORGANISM: human

<400> SEQUENCE: 71
caucccuugc augguggagg g                                                 21

<210> SEQ ID NO 72
<211> LENGTH: 22
<212> TYPE: RNA
<213> ORGANISM: human

<400> SEQUENCE: 72
ugauauguuu gauauauuag gu                                                22
```

<210> SEQ ID NO 73
<211> LENGTH: 23
<212> TYPE: RNA
<213> ORGANISM: human

<400> SEQUENCE: 73
caacggaauc ccaaaagcag cug                                              23

<210> SEQ ID NO 74
<211> LENGTH: 21
<212> TYPE: RNA
<213> ORGANISM: human

<400> SEQUENCE: 74
cugaccuaug aauugacagc c                                                21

<210> SEQ ID NO 75
<211> LENGTH: 22
<212> TYPE: RNA
<213> ORGANISM: human

<400> SEQUENCE: 75
ugggucuuug cgggcgagau ga                                               22

<210> SEQ ID NO 76
<211> LENGTH: 22
<212> TYPE: RNA
<213> ORGANISM: human

<400> SEQUENCE: 76
uguaacagca acuccaugug ga                                               22

<210> SEQ ID NO 77
<211> LENGTH: 21
<212> TYPE: RNA
<213> ORGANISM: human

<400> SEQUENCE: 77
uagcagcaca gaaauauugg c                                                21

<210> SEQ ID NO 78
<211> LENGTH: 22
<212> TYPE: RNA
<213> ORGANISM: human

<400> SEQUENCE: 78
uagguaguuu cauguuguug gg                                               22

<210> SEQ ID NO 79
<211> LENGTH: 22
<212> TYPE: RNA
<213> ORGANISM: human

<400> SEQUENCE: 79
uagguaguuu ccuguuguug gg                                               22

<210> SEQ ID NO 80
<211> LENGTH: 22
<212> TYPE: RNA
<213> ORGANISM: human

<400> SEQUENCE: 80
uucaccaccu ucuccaccca gc                                               22

```
<210> SEQ ID NO 81
<211> LENGTH: 22
<212> TYPE: RNA
<213> ORGANISM: human

<400> SEQUENCE: 81
gguccagagg ggagauaggu uc                                              22

<210> SEQ ID NO 82
<211> LENGTH: 23
<212> TYPE: RNA
<213> ORGANISM: human

<400> SEQUENCE: 82
cccaguguuc agacuaccug uuc                                             23

<210> SEQ ID NO 83
<211> LENGTH: 23
<212> TYPE: RNA
<213> ORGANISM: human

<400> SEQUENCE: 83
cccaguguuu agacuaucug uuc                                             23

<210> SEQ ID NO 84
<211> LENGTH: 22
<212> TYPE: RNA
<213> ORGANISM: human

<400> SEQUENCE: 84
aguuuugcau aguugcacua ca                                              22

<210> SEQ ID NO 85
<211> LENGTH: 23
<212> TYPE: RNA
<213> ORGANISM: human

<400> SEQUENCE: 85
ugugcaaauc caugcaaaac uga                                             23

<210> SEQ ID NO 86
<211> LENGTH: 23
<212> TYPE: RNA
<213> ORGANISM: human

<400> SEQUENCE: 86
uaaagugcuu auagugcagg uag                                             23

<210> SEQ ID NO 87
<211> LENGTH: 22
<212> TYPE: RNA
<213> ORGANISM: human

<400> SEQUENCE: 87
uaacacuguc ugguaacgau gu                                              22

<210> SEQ ID NO 88
<211> LENGTH: 22
<212> TYPE: RNA
<213> ORGANISM: human

<400> SEQUENCE: 88
```

-continued uaauacugcc ugguaaugau ga                    22

<210> SEQ ID NO 89
<211> LENGTH: 23
<212> TYPE: RNA
<213> ORGANISM: human

<400> SEQUENCE: 89
uaauacugcc ggguaaugau gga                   23

<210> SEQ ID NO 90
<211> LENGTH: 22
<212> TYPE: RNA
<213> ORGANISM: human

<400> SEQUENCE: 90
gugaaauguu uaggaccacu ag                    22

<210> SEQ ID NO 91
<211> LENGTH: 22
<212> TYPE: RNA
<213> ORGANISM: human

<400> SEQUENCE: 91
uucccuuugu cauccuaugc cu                    22

<210> SEQ ID NO 92
<211> LENGTH: 22
<212> TYPE: RNA
<213> ORGANISM: human

<400> SEQUENCE: 92
uccuucauuc caccggaguc ug                    22

<210> SEQ ID NO 93
<211> LENGTH: 22
<212> TYPE: RNA
<213> ORGANISM: human

<400> SEQUENCE: 93
uggaauguaa ggaagugugu gg                    22

<210> SEQ ID NO 94
<211> LENGTH: 22
<212> TYPE: RNA
<213> ORGANISM: human

<400> SEQUENCE: 94
auaagacgag caaaaagcuu gu                    22

<210> SEQ ID NO 95
<211> LENGTH: 22
<212> TYPE: RNA
<213> ORGANISM: human

<400> SEQUENCE: 95
uagcuuauca gacugauguu ga                    22

<210> SEQ ID NO 96
<211> LENGTH: 22
<212> TYPE: RNA
<213> ORGANISM: human

<400> SEQUENCE: 96

-continued cugugcgugu gacagcggcu ga                                             22

<210> SEQ ID NO 97
<211> LENGTH: 22
<212> TYPE: RNA
<213> ORGANISM: human

<400> SEQUENCE: 97
uucccuuugu cauccuucgc cu                                             22

<210> SEQ ID NO 98
<211> LENGTH: 21
<212> TYPE: RNA
<213> ORGANISM: human

<400> SEQUENCE: 98
uaacagucuc cagucacggc c                                              21

<210> SEQ ID NO 99
<211> LENGTH: 22
<212> TYPE: RNA
<213> ORGANISM: human

<400> SEQUENCE: 99
acagcaggca cagacaggca gu                                             22

<210> SEQ ID NO 100
<211> LENGTH: 21
<212> TYPE: RNA
<213> ORGANISM: human

<400> SEQUENCE: 100
augaccuaug aauugacaga c                                              21

<210> SEQ ID NO 101
<211> LENGTH: 22
<212> TYPE: RNA
<213> ORGANISM: human

<400> SEQUENCE: 101
uaaucucagc uggcaacugu ga                                             22

<210> SEQ ID NO 102
<211> LENGTH: 23
<212> TYPE: RNA
<213> ORGANISM: human

<400> SEQUENCE: 102
uacugcauca ggaacugauu gga                                            23

<210> SEQ ID NO 103
<211> LENGTH: 21
<212> TYPE: RNA
<213> ORGANISM: human

<400> SEQUENCE: 103
uugugcuuga ucuaaccaug u                                              21

<210> SEQ ID NO 104
<211> LENGTH: 21
<212> TYPE: RNA
<213> ORGANISM: human

```
<400> SEQUENCE: 104
ugauugucca aacgcaauuc u                                              21

<210> SEQ ID NO 105
<211> LENGTH: 22
<212> TYPE: RNA
<213> ORGANISM: human

<400> SEQUENCE: 105
aagcugccag uugaagaacu gu                                             22

<210> SEQ ID NO 106
<211> LENGTH: 21
<212> TYPE: RNA
<213> ORGANISM: human

<400> SEQUENCE: 106
ccacaccgua ucugacacuu u                                              21

<210> SEQ ID NO 107
<211> LENGTH: 23
<212> TYPE: RNA
<213> ORGANISM: human

<400> SEQUENCE: 107
agcuacauug ucugcugggu uuc                                            23

<210> SEQ ID NO 108
<211> LENGTH: 21
<212> TYPE: RNA
<213> ORGANISM: human

<400> SEQUENCE: 108
agcuacaucu ggcuacuggg u                                              21

<210> SEQ ID NO 109
<211> LENGTH: 22
<212> TYPE: RNA
<213> ORGANISM: human

<400> SEQUENCE: 109
ugucaguuug ucaaauaccc ca                                             22

<210> SEQ ID NO 110
<211> LENGTH: 21
<212> TYPE: RNA
<213> ORGANISM: human

<400> SEQUENCE: 110
caagucacua gugguuccgu u                                              21

<210> SEQ ID NO 111
<211> LENGTH: 1340
<212> TYPE: DNA
<213> ORGANISM: Human
<220> FEATURE:
<223> OTHER INFORMATION: EPO

<400> SEQUENCE: 111
cccggagccg gaccggggcc accgcgcccg ctctgctccg acaccgcgcc cctggacag    60 ccgccctctc ctccaggccc gtggggctgg ccctgcaccg ccgagcttcc cgggatgagg  120
gcccccggtg tggtcacccg gcgcgcccca ggtcgctgag ggaccccggc caggcgcgga  180
```

```
gatgggggtg cacgaatgtc ctgcctggct gtggcttctc ctgtccctgc tgtcgctccc      240
tctgggcctc ccagtcctgg gcgccccacc acgcctcatc tgtgacagcc gagtcctgga      300
gaggtacctc ttggaggcca aggaggccga gaatatcacg acgggctgtg ctgaacactg      360
cagcttgaat gagaatatca ctgtcccaga caccaaagtt aatttctatg cctggaagag      420
gatggaggtc gggcagcagg ccgtagaagt ctggcagggc ctggccctgc tgtcggaagc      480
tgtcctgcgg ggccaggccc tgttggtcaa ctcttcccag ccgtgggagc cctgcagct       540 gcatgtggat aaagccgtca gtggccttcg cagcctcacc actctgcttc gggctctggg      600
agcccagaag gaagccatct cccctccaga tgcggcctca gctgctccac tccgaacaat      660
cactgctgac actttccgca aactcttccg agtctactcc aatttcctcc ggggaaagct      720
gaagctgtac acaggggagg cctgcaggac aggggacaga tgaccaggtg tgtccacctg      780
ggcatatcca ccacctccct caccaacatt gcttgtgcca caccctcccc cgccactcct      840 gaacccgtc gaggggctct cagctcagcg ccagcctgtc ccatggacac tccagtgcca       900
gcaatgacat ctcaggggcc agaggaactg tccagagagc aactctgaga tctaaggatg      960
tcacagggcc aacttgaggg cccagagcag gaagcattca gagagcagct ttaaactcag     1020
ggacagagcc atgctgggaa gacgcctgag ctcactcggc accctgcaaa atttgatgcc     1080
aggacacgct ttggaggcga tttacctgtt ttcgcaccta ccatcaggga caggatgacc     1140
tggagaactt aggtggcaag ctgtgacttc tccaggtctc acgggcatgg gcactccctt     1200
ggtggcaaga gccccctga caccggggtg gtgggaacca tgaagacagg atgggggctg      1260
gcctctggct ctcatggggt ccaagttttg tgtattcttc aacctcattg acaagaactg     1320
aaaccaccaa aaaaaaaaa                                                 1340

<210> SEQ ID NO 112
<211> LENGTH: 582
<212> TYPE: DNA
<213> ORGANISM: human
<220> FEATURE:
<223> OTHER INFORMATION: EPO ORF

<400> SEQUENCE: 112 atggggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagag      240 atggaggtcg ggcagcaggc cgtagaagtc tggcagggcc tggccctgct gtcggaagct     300
gtcctgcggg gccaggccct gttggtcaac tcttcccagc cgtgggagcc ctgcagctg      360 catgtggata aagccgtcag tggccttcgc agcctcacca ctctgcttcg ggctctggga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacagat ga                         582

<210> SEQ ID NO 113
<211> LENGTH: 1340
<212> TYPE: DNA
<213> ORGANISM: human
<220> FEATURE:
<223> OTHER INFORMATION: EPO modified
```

<400> SEQUENCE: 113

```
cccggagccg gaccggggcc accgcgcccg ctctactccg acaccgcgcc ccctagacag        60
ccgccctctc ctccaggccc gtagggctag ccctacaccg ccgagcttcc cgggttaagg       120
gcccccggtc tagtcacccg gcgcgcccca ggtcgctaag ggaccccggc caggcgcgga       180
gatgggggta cacaattatc ctacctagct ctagcttctc ctatccctac tatcgctccc       240
tctaggcctc ccagtcctag gcgccccacc acacctcctc tttaacagcc gagtcctaga       300
gaggtacctc ttagaggcca aggaggccga gaatatcacg acgggctgtg ctgaacactg       360
cagcttgatt aagattttaa ctatcccaga caccaaagtt attatcttta cctagaagag       420
gttagaggtc gggcagcagg ccgtagaagt ctagcagggc ctagccctac tatcggaagc       480
tgtcctacgg ggccaggccc tattagtcaa ctcttcccag ccgtaggagc ccctacagct       540
gcctctagtt aaagccgtca gtagccttcg cagcctcacc actctacttc gggctctagg       600
agcccagaag gaagccctct cccctccagt tacggcctca gctactccac tccgaacaat       660
cactactaac actttccgca aactcttccg agtctactcc aatatcctcc ggggaaagct       720
gaagctatac acaggggagg cctacaggac aggggacagt taaccagttt tatccaccta       780
ggcttttaca ccacctccct caccaactta ccttttacca cccctcccc cgccactcct        840
gaacccgtc gagggctct cagctcagcg ccagcctatc ccttagacac tccagtacca        900
gcattaactt atcaggggcc agaggaacta tccagagagc aactctaagt tataaggtta       960
tcacagggcc aacttaaggg cccagagcag gaagcttaca gagagcagct ttaaactcag      1020
ggacagagcc ttactaggaa gacacctaag ctcactcggc accctacaaa ttttattacc      1080
aggacacact ttagaggcgt tatacctatt ttcgcaccta ccttaaggga caggttaacc      1140
tggagaactt aggtagcaag ctctcacttc tccaggtctc acaggcttag gcactccctt      1200
ggtagcaaga gccccttaa caccggggta gtaggaacct aaagacagg ttaggggcta       1260
gcctctagct ctcttagggt ccaagttctt tatttacttc aacctcttac acaagaacta      1320
aaaccaccaa aaaaaaaaaa                                                  1340
```

<210> SEQ ID NO 114
<211> LENGTH: 21
<212> TYPE: RNA
<213> ORGANISM: human

<400> SEQUENCE: 114

```
uucaaguaau ucaggauagg u                                                 21
```

<210> SEQ ID NO 115
<211> LENGTH: 582
<212> TYPE: DNA
<213> ORGANISM: human
<220> FEATURE:
<223> OTHER INFORMATION: EPO ORF modified

<400> SEQUENCE: 115

```
atgggggtcc acgagtgtcc cgcttggctt tggcttctcc tctccctcct ctcgctccct        60
ctcggcctcc cagtcctcgg cgccccaccc gcctcatttt gcgacagccg agtcctcgag       120
aggtacctcc tagaggccaa ggaggccgag aacatcacaa ctggttgcgc cgaacattgc       180
agccttaacg agaacatcac agtcccagac accaaagtta acttctacgc ttggaagcgg       240
atggaggtcg ggcagcaggc cgtagaggtt tggcagggcc tcgccctcct ctcggaagcc       300
gtcctccggg gccaggccct cctagtcaac tcttcccagc cgtgggagcc cctccagctc       360
```

```
cacgtcgaca aagccgtcag cggccttcgc agcctcacca ctctccttcg ggctctcgga    420
gcccagaagg aagccatctc ccctccagac gcggcctcag ccgctccact ccgaacaatc    480
acagccgaca ctttccgcaa actcttccga gtctactcca acttcctccg gggaaagctc    540
aagctctaca caggggaggc ttgcaggaca ggggaccgtt ga                      582

<210> SEQ ID NO 116
<211> LENGTH: 582
<212> TYPE: DNA
<213> ORGANISM: human
<220> FEATURE:
<223> OTHER INFORMATION: EPO ORF modified signal peptide

<400> SEQUENCE: 116 atggggtcc acgagtgtcc cgcttggctt tggcttctcc tctccctcct ctcgctccct      60
ctcggcctcc cagtcctcgg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata aagccgtcag tggccttcgc agcctcacca ctctgcttcg ggctctggga    420
gcccagaagg aagccatctc ccctccagat gcggcctcag ctgctccact ccgaacaatc    480
actgctgaca ctttccgcaa actcttccga gtctactcca atttcctccg gggaaagctg    540
aagctgtaca caggggaggc ctgcaggaca ggggacagat ga                      582

<210> SEQ ID NO 117
<211> LENGTH: 582
<212> TYPE: DNA
<213> ORGANISM: human
<220> FEATURE:
<223> OTHER INFORMATION: EPO ORF modified signal peptide

<400> SEQUENCE: 117 atggggtgc acgagtgtcc cgcttggctt tggcttctcc tctccctcct ctcgctccct      60
ctcggcctcc cagtcctcgg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata aagccgtcag tggccttcgc agcctcacca ctctgcttcg ggctctggga    420
gcccagaagg aagccatctc ccctccagat gcggcctcag ctgctccact ccgaacaatc    480
actgctgaca ctttccgcaa actcttccga gtctactcca atttcctccg gggaaagctg    540
aagctgtaca caggggaggc ctgcaggaca ggggacagat ga                      582

<210> SEQ ID NO 118
<211> LENGTH: 582
<212> TYPE: DNA
<213> ORGANISM: human
<220> FEATURE:
<223> OTHER INFORMATION: EPO ORF modified signal peptide

<400> SEQUENCE: 118
```

```
atgggggtgc accagtgtcc cgcttggctt tggcttctcc tctccctcct ctcgctccct    60
ctcggcctcc cagtcctcgg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata agccgtcag tggccttcgc agcctcacca ctctgcttcg ggctctggga   420
gcccagaagg aagccatctc ccctccagat gcggcctcag ctgctccact ccgaacaatc   480
actgctgaca ctttccgcaa actcttccga gtctactcca atttcctccg ggaaagctg    540 aagctgtaca caggggaggc ctgcaggaca ggggacagat ga                      582
```

<210> SEQ ID NO 119
<211> LENGTH: 582
<212> TYPE: DNA
<213> ORGANISM: human
<220> FEATURE:
<223> OTHER INFORMATION: EPO ORF modified signal peptide

<400> SEQUENCE: 119

```
atgggggtga gggagtgtcc cgcttggctt tggcttctcc tctccctcct ctcgctccct    60
ctcggcctcc cagtcctcgg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata agccgtcag tggccttcgc agcctcacca ctctgcttcg ggctctggga   420
gcccagaagg aagccatctc ccctccagat gcggcctcag ctgctccact ccgaacaatc   480
actgctgaca ctttccgcaa actcttccga gtctactcca atttcctccg ggaaagctg    540 aagctgtaca caggggaggc ctgcaggaca ggggacagat ga                      582
```

<210> SEQ ID NO 120
<211> LENGTH: 660
<212> TYPE: DNA
<213> ORGANISM: E. coli
<220> FEATURE:
<223> OTHER INFORMATION: Reporter vector pCAT<R>3-Control vector

<400> SEQUENCE: 120

```
atggagaaaa aaatcactgg atataccacc gttgatatat cccaatggca tcgtaaagaa    60
cattttgagg catttcagtc agttgctcaa tgtacctata accagaccgt tcagctggat   120
attacggcct ttttaaagac cgtaaagaaa aataagcaca gtttttatcc ggcctttatt   180
cacattcttg cccgcctgat gaatgctcat ccggaattcc gtatggcaat gaaagacggt   240
gagctggtga tatgggatag tgttcaccct tgttacaccg ttttccatga gcaaactgaa   300
acgttttcat cgctctggag tgaataccac gacgatttcc ggcagtttct acacatatat   360
tcgcaagatg tggcgtgtta cggtgaaaac ctggcctatt tccctaaagg gtttattgag   420
aatatgtttt tcgtctcagc caatccctgg gtgagtttca ccagttttga tttaaacgtg   480
gccaatatgg acaacttctt cgcccccgtt ttcaccatgg gcaaatatta tacgcaaggc   540
gacaaggtgc tgatgccgct ggcgattcag gttcatcatg ccgtttgtga tggcttccat   600
```

```
gtcggcagaa tgcttaatga attacaacag tactgcgatg agtggcaggg cggggcgtaa    660
```

<210> SEQ ID NO 121
<211> LENGTH: 660
<212> TYPE: DNA
<213> ORGANISM: E. coli
<220> FEATURE:
<223> OTHER INFORMATION: modified reporter vector pCAT<R>3-Control
      vector

<400> SEQUENCE: 121

```
atggagaaaa aaatcacagg ctataccacc gtcgacataa gccagtggca ccgtaaagaa     60
cacttcgagg cttttcagtc agtcgctcag tgtacctaca accagaccgt tcagctcgac    120
atcacagcct ttttaaaaac cgtaaaaaaa aacaaacaca agttttaccc ggcctttatc    180
cacatcctcg cccgcctgat gaacgctcac ccggagttcc gtatggcaat gaaagacggg    240
gagctcgtca tctgggacag cgttcacccc tgttacaccg ttttccacga gcaaacagaa    300
acttttcttt cgctttggtc agagtaccac gacgacttcc ggcagtttct acacatctac    360
tcgcaagacg tcgcctgtta cggggaaaac ctcgcctact tccctaaagg gtttatcgag    420
aacatgtttt tcgtctcagc caaccccctgg gtcagtttca ccagtttcga cttaaacgta    480
gccaacatgg acaacttctt cgcccccgtt ttcaccatgg gcaagtacta cactcaaggc    540
gacaaagtcc tcatgccgct cgcgatccag gttcaccacg ccgtctgcga cggcttccac    600
gtcggccgga tgcttaacga gttacaacag tactgcgacg agtggcaggg cggggcgtaa    660
```

<210> SEQ ID NO 122
<211> LENGTH: 660
<212> TYPE: DNA
<213> ORGANISM: E. coli
<220> FEATURE:
<223> OTHER INFORMATION: partially modified reporter vector pCAT<R>3-
      Control vector

<400> SEQUENCE: 122

```
atggagaaaa aaatcacagg ctataccacc gtcgacataa gccagtggca ccgtaaagaa     60
cacttcgagg cttttcagtc agtcgctcag tgtacctaca accagaccgt tcagctggat    120
attacggcct ttttaaagac cgtaaagaaa aataagcaca agttttatcc ggcctttatt    180
cacattcttg cccgcctgat gaatgctcat ccggaattcc gtatggcaat gaaagacggg    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatcccctgg gtgagtttca ccagtttga tttaaacgtg    480 gccaatatgg acaacttctt cgcccccgtt ttcaccatgg gcaaatatta tacgcaaggc    540
gacaaggtgc tgatgccgct ggcgattcag gttcatcatg ccgtttgtga tggcttccat    600
gtcggcagaa tgcttaatga attacaacag tactgcgatg agtggcaggg cggggcgtaa    660
```

<210> SEQ ID NO 123
<211> LENGTH: 65
<212> TYPE: DNA
<213> ORGANISM: human
<220> FEATURE:
<223> OTHER INFORMATION: CD5 signal peptide sequence

<400> SEQUENCE: 123

```
atgcccatgg ggtctctgca accgctggcc accttgtacc tgctggggat gctggtcgct    60
tccgt                                                                65

<210> SEQ ID NO 124
<211> LENGTH: 65
<212> TYPE: DNA
<213> ORGANISM: human
<220> FEATURE:
<223> OTHER INFORMATION: CD5 signal peptide sequence modified

<400> SEQUENCE: 124
atgcccatcg ggtctctgca accgctggcc accttgtacc tgctggggat cctggtcgct    60
tccgt                                                                65

<210> SEQ ID NO 125
<211> LENGTH: 65
<212> TYPE: DNA
<213> ORGANISM: human
<220> FEATURE:
<223> OTHER INFORMATION: CD5 signal peptide sequence modified

<400> SEQUENCE: 125
atgcccatgg ggtctctcca accgctcgcc accttgtacc tcctcgggat gctcgtcgct    60
tccgt                                                                65

<210> SEQ ID NO 126
<211> LENGTH: 65
<212> TYPE: DNA
<213> ORGANISM: human
<220> FEATURE:
<223> OTHER INFORMATION: CD5 signal peptide sequence modified

<400> SEQUENCE: 126
atgcccatcg ggtctctcca accgctcgcc accttgtacc tcctcgggat cctcgtcgct    60
tccgt                                                                65

<210> SEQ ID NO 127
<211> LENGTH: 65
<212> TYPE: DNA
<213> ORGANISM: human
<220> FEATURE:
<223> OTHER INFORMATION: CD5 signal peptide sequence modified

<400> SEQUENCE: 127
atggctatcg ggtctctcca accgctcgcc accttgtacc tcctcgggat cctcgtcgct    60
tccgt                                                                65

<210> SEQ ID NO 128
<211> LENGTH: 738
<212> TYPE: DNA
<213> ORGANISM: human
<220> FEATURE:
<223> OTHER INFORMATION: Anti Thy-VL ORF containing light chain signal
      peptide 1

<400> SEQUENCE: 128
atggacatga gggtccccgc tcagctcctg gggctcctgc tgctctggct cccaggtgcc    60
agatgtgata tcctcgtgat gacccagtct ccagtcaccc tgtctttgtc ttcaggggaa   120
agagccaccc tctcctgcag ggccagtcag agtattagta actccttagc ctggtaccaa   180
cagaaacctg gcctggctcc caggctcctc atctatgatg catccaacag ggccactggc   240
```

| gtcccagcca | ggttcagtgg | cagtgggtct | gggacagact | tcaatctcac | catcagcagc | 300 |
| ttcaatctca | ccatcagcag | cctagaccct | gaagatgttg | cagtgtatta | ctgtcaccag | 360 |
| cgtagcaact | ggcctccttt | cactttcggc | ggagggacca | aggtggagat | caaacgtacg | 420 |
| gtggctgcac | catctgtctt | catcttcccg | ccatctgatg | agcagttgaa | atctggaact | 480 |
| gcctctgttg | tgtgcctgct | gaataacttc | tatcccagag | aggccaaagt | acagtggaag | 540 |
| gtggataacg | ccctccaatc | gggtaactcc | caggagagtg | tcacagagca | ggacagcaag | 600 |
| gacagcacct | acagcctcag | cagcaccctg | acgctgagca | aagcagacta | cgagaaacac | 660 |
| aaagtctacg | cctgcgaagt | cacccatcag | ggcctgagct | cgcccgtcac | aaagagcttc | 720 |
| aacaggggag | agtgttag | | | | | 738 |

<210> SEQ ID NO 129
<211> LENGTH: 738
<212> TYPE: DNA
<213> ORGANISM: human
<220> FEATURE:
<223> OTHER INFORMATION: Anti Thy-VL ORF containing light chain signal
      peptide 1mod

<400> SEQUENCE: 129

| atggacatca | gggtccccgc | tcagctcctc | gggctcctcc | tcctttggct | cccaggtgcc | 60 |
| aggtgtgata | tcctcgtgat | gacccagtct | ccagtcaccc | tgtctttgtc | ttcaggggaa | 120 |
| agagccaccc | tctcctgcag | ggccagtcag | agtattagta | actccttagc | ctggtaccaa | 180 |
| cagaaacctg | gctggctcc | caggctcctc | atctatgatg | catccaacag | ggccactggc | 240 |
| gtcccagcca | ggttcagtgg | cagtgggtct | gggacagact | tcaatctcac | catcagcagc | 300 |
| ttcaatctca | ccatcagcag | cctagaccct | gaagatgttg | cagtgtatta | ctgtcaccag | 360 |
| cgtagcaact | ggcctccttt | cactttcggc | ggagggacca | aggtggagat | caaacgtacg | 420 |
| gtggctgcac | catctgtctt | catcttcccg | ccatctgatg | agcagttgaa | atctggaact | 480 |
| gcctctgttg | tgtgcctgct | gaataacttc | tatcccagag | aggccaaagt | acagtggaag | 540 |
| gtggataacg | ccctccaatc | gggtaactcc | caggagagtg | tcacagagca | ggacagcaag | 600 |
| gacagcacct | acagcctcag | cagcaccctg | acgctgagca | aagcagacta | cgagaaacac | 660 |
| aaagtctacg | cctgcgaagt | cacccatcag | ggcctgagct | cgcccgtcac | aaagagcttc | 720 |
| aacaggggag | agtgttag | | | | | 738 |

<210> SEQ ID NO 130
<211> LENGTH: 732
<212> TYPE: DNA
<213> ORGANISM: human
<220> FEATURE:
<223> OTHER INFORMATION: Anti Thy-VL ORF containing light chain signal
      peptide 2

<400> SEQUENCE: 130

| atgagggtcc | ccgcgctgct | cctggggctg | ctaatgctct | ggatacctgg | atctagtgca | 60 |
| gatatcctcg | tgatgaccca | gtctccagtc | accctgtctt | tgtcttcagg | ggaaagagcc | 120 |
| accctctcct | gcagggccag | tcagagtatt | agtaactcct | tagcctggta | ccaacagaaa | 180 |
| cctggcctgg | ctcccaggct | cctcatctat | gatgcatcca | acagggccac | tggcgtccca | 240 |
| gccaggttca | gtggcagtgg | gtctgggaca | gacttcaatc | tcaccatcag | cagcttcaat | 300 |
| ctcaccatca | gcagcctaga | ccctgaagat | gttgcagtgt | attactgtca | ccagcgtagc | 360 |
| aactggcctc | ctttcacttt | cggcggaggg | accaaggtgg | agatcaaacg | tacggtggct | 420 |

```
gcaccatctg tcttcatctt cccgccatct gatgagcagt tgaaatctgg aactgcctct    480
gttgtgtgcc tgctgaataa cttctatccc agagaggcca agtacagtg gaaggtggat     540 aacgccctcc aatcgggtaa ctcccaggag agtgtcacag agcaggacag caaggacagc    600
acctacagcc tcagcagcac cctgacgctg agcaaagcag actacgagaa acacaaagtc    660
tacgcctgcg aagtcaccca tcagggcctg agctcgcccg tcacaaagag cttcaacagg    720
ggagagtgtt ag                                                        732

<210> SEQ ID NO 131
<211> LENGTH: 1640
<212> TYPE: DNA
<213> ORGANISM: human
<220> FEATURE:
<223> OTHER INFORMATION: Anti Thy-VH containing heavy chain signal
      peptide 1

<400> SEQUENCE: 131
atggactgga cctggaggtt cctctttgtg gtggcagcag ctacaggtgt ccagtcccag      60
gtgcaattgc tcgaggagtc gggggctgag ttgaagaagc ctgggggcctc agtgaaggtc    120 tcctgcaagg cttctggata caccttcacc gcctactaca tacactgggt gcgtcaggcc    180
cctggacaag gcttgagtg gatgggatgg atcaaccta acagtggtgg cacaaactat      240
gcacagaagt ttcagggcag ggtcaccatg accaggaca cgtccagcag cacagcctac     300
atggacctga gcaggctgac atctgacgac acggccgtct attactgtgc gcgagaaaat    360
ggtcctttaa acaccgcctt cttctacggt ttggacgtct ggggccaagg gacactagtc    420
accgtctcct cagcctccac caagggccca tcggtcttcc ccctggcacc ctcctccaag    480
agcacctctg gggggcacagc ggccctgggc tgcctggtca aggactactt ccccgaaccg   540
gtgacggtgt cgtggaactc aggcgccctg accagcggcg tgcacacctt cccggctgtc    600
ctacagtcct caggactcta ctccctcagc agcgtggtga ccgtgccctc agcagcttg    660 ggcacccaga cctacatctg caacgtgaat cacaagccca gcaacaccaa ggtcgacaag    720
aaagttgagc ccaaatcttc tgacaaaact cacacatgcc caccgtgccc aggtaagcca    780
gcccaggcct cgccctccag ctcaaggcgg gacaggtgcc ctagagtagc ctgcatccag    840
ggacaggccc cagccgggtg ctgacacgtc cacctccatc tcttcctcag cacctgaact    900
cctgggggga ccgtcagtct cctcttcccc ccaaaaccc aaggacaccc tcatgatctc     960
ccggacccct gaggtcacat gcgtggtggt ggacgtgagc cacgaagacc ctgaggtcaa   1020
gttcaactgg tacgtggacg gcgtggaggt gcataatgcc aagacaaagc cgcgggagga   1080
gcagtacaac agcacgtacc gtgtggtcag cgtcctcacc gtcctgcacc aggactggct   1140
gaatggcaag gagtacaagt gcaaggtctc caacaaagcc ctcccagccc ccatcgagaa   1200
aaccatctcc aaagccaaag gtgggacccg tggggtgcga gggccacatg gacagaggcc   1260
ggctcggccc accctctgcc ctgagagtga ccgctgtacc aacctctgtc cctacagggc   1320
agccccgaga accacaggtg tacaccctgc ccccatcacg ggaggagatg accaagaacc   1380
aggtcagcct gacctgcctg gtcaaaggct tctatcccag cgacatcgcc gtggagtggg   1440
agagcaatgg gcagccggag aacaactaca agaccacgcc tcccgtgctg gactccgacg   1500
gctccttctt cctctatagc aagctcaccg tggacaagag caggtggcag caggggaacg   1560
tcttctcatg ctccgtgatg catgaggctc tgcacaacca ctacacgcag aagagcctct   1620
ccctgtcccc gggtaaataa                                               1640
```

<210> SEQ ID NO 132
<211> LENGTH: 1640
<212> TYPE: DNA
<213> ORGANISM: human
<220> FEATURE:
<223> OTHER INFORMATION: Anti Thy-VH containing heavy chain signal
      peptide 1 mod

<400> SEQUENCE: 132

```
atggattgga cttggaggtt cctctttgtg gtggcagcag ctacaggtgt ccagtcccag     60
gtgcaattgc tcgaggagtc gggggctgag ttgaagaagc ctggggcctc agtgaaggtc    120
tcctgcaagg cttctggata caccttcacc gcctactaca tacactgggt gcgtcaggcc    180
cctggacaag gcttgagtg gatgggatgg atcaaccta acagtggtgg cacaaactat      240
gcacagaagt tcagggcag gtcaccatg accagggaca cgtccagcag cacagcctac     300
atggacctga gcaggctgac atctgacgac acggccgtct attactgtgc gcgagaaaat   360
ggtcctttaa acaccgcctt cttctacggt ttggacgtct ggggccaagg gacactagtc    420
accgtctcct cagcctccac caagggccca tcggtcttcc cctggcacc ctcctccaag     480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg     660
ggcacccaga cctacatctg caacgtgaat cacaagccca gcaacaccaa ggtcgacaag    720
aaagttgagc ccaaatcttc tgacaaaact cacacatgcc caccgtgccc aggtaagcca    780
gcccaggcct cgccctccag ctcaaggcgg gacaggtgcc ctagagtagc ctgcatccag    840
gacaggccc cagccgggtg ctgacacgtc cacctccatc tcttcctcag cacctgaact    900
cctgggggga ccgtcagtct cctcttccc ccaaaaccc aaggacaccc tcatgatctc      960
ccggaccct gaggtcacat gcgtggtggt ggacgtgagc cacgaagacc ctgaggtcaa    1020
gttcaactgg tacgtggacg gcgtggaggt gcataatgcc aagacaaagc cgcgggagga  1080
gcagtacaac agcacgtacc gtgtggtcag cgtcctcacc gtcctgcacc aggactggct  1140
gaatggcaag gagtacaagt gcaaggtctc caacaaagcc ctcccagccc ccatcgagaa  1200
aaccatctcc aaagccaaag gtgggaccg tggggtgcga gggccacatg gacagaggcc   1260
ggctcggccc accctctgcc ctgagagtga ccgctgtacc aacctctgtc cctacagggc  1320
agccccgaga accacaggtg tacacccgc ccccatcacg ggaggagatg accaagaacc    1380
aggtcagcct gacctgcctg gtcaaaggct tctatcccag cgacatcgcc gtggagtggg  1440
agagcaatgg gcagccggag aacaactaca agaccacgcc tcccgtgctg gactccgacg  1500
gctccttctt cctctatagc aagctcaccg tggacaagag caggtggcag caggggaacg  1560
tcttctcatg ctccgtgatg catgaggctc tgcacaacca ctacacgcag aagagcctct  1620
ccctgtcccc gggtaaataa                                              1640
```

<210> SEQ ID NO 133
<211> LENGTH: 1640
<212> TYPE: DNA
<213> ORGANISM: human
<220> FEATURE:
<223> OTHER INFORMATION: Anti Thy-VH containing heavy chain signal
      peptide 2

<400> SEQUENCE: 133

| | |
|---|---|
| atggattgga cttggaggtt cctctttgtg gtggcagcag ctacaggtgt ccagtcccag | 60 |
| gtgcaattgc tcgaggagtc gggggctgag ttgaagaagc tggggcctc agtgaaggtc | 120 |
| tcctgcaagg cttctggata caccttcacc gcctactaca tacactgggt gcgtcaggcc | 180 |
| cctggacaag gcttgagtg gatgggatgg atcaaccta acagtggtgg cacaaactat | 240 |
| gcacagaagt ttcagggcag ggtcaccatg accagggaca cgtccagcag cacagcctac | 300 |
| atggacctga gcaggctgac atctgacgac acggccgtct attactgtgc gcgagaaaat | 360 |
| ggtcctttaa acaccgcctt cttctacggt ttggacgtct ggggccaagg gacactagtc | 420 |
| accgtctcct cagcctccac caagggccca tcggtcttcc ccctggcacc ctcctccaag | 480 |
| agcacctctg ggggcacagc ggccctgggc tgcctggtca aggactactt ccccgaaccg | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc cagcagcttg | 660 |
| ggcacccaga cctacatctg caacgtgaat cacaagccca gcaacaccaa ggtcgacaag | 720 |
| aaagttgagc ccaaatcttc tgacaaaact cacacatgcc caccgtgccc aggtaagcca | 780 |
| gcccaggcct cgccctccag ctcaaggcgg acaggtgcc ctagagtagc ctgcatccag | 840 |
| gacaggccc cagccgggtg ctgacacgtc cacctccatc tcttcctcag cacctgaact | 900 |
| cctgggggga ccgtcagtct tcctcttccc cccaaaaccc aaggacaccc tcatgatctc | 960 |
| ccggaccct gaggtcacat gcgtggtggt ggacgtgagc cacgaagacc ctgaggtcaa | 1020 |
| gttcaactgg tacgtggacg gcgtggaggt gcataatgcc aagacaaagc cgcgggagga | 1080 |
| gcagtacaac agcacgtacc gtgtggtcag cgtcctcacc gtcctgcacc aggactggct | 1140 |
| gaatggcaag gagtacaagt gcaaggtctc caacaaagcc ctcccagccc ccatcgagaa | 1200 |
| aaccatctcc aaagccaaag gtgggacccg tggggtgcga gggccacatg gacagaggcc | 1260 |
| ggctcggccc accctctgcc ctgagagtga ccgctgtacc aacctctgtc cctacagggc | 1320 |
| agccccgaga accacaggtg tacaccctgc cccatcacg ggaggagatg accaagaacc | 1380 |
| aggtcagcct gacctgcctg gtcaaaggct tctatcccag cgacatcgcc gtggagtggg | 1440 |
| agagcaatgg gcagccggag aacaactaca agaccacgcc tcccgtgctg gactccgacg | 1500 |
| gctccttctt cctctatagc aagctcaccg tggacaagag caggtggcag caggggaacg | 1560 |
| tcttctcatg ctccgtgatg catgaggctc tgcacaacca ctacacgcag aagagcctct | 1620 |
| ccctgtcccc gggtaaataa | 1640 |

<210> SEQ ID NO 134
<211> LENGTH: 687
<212> TYPE: DNA
<213> ORGANISM: Artificial sequence
<220> FEATURE:
<223> OTHER INFORMATION: HcRed1 ORF Reef Coral - human codon optimized

<400> SEQUENCE: 134

| | |
|---|---|
| atggtgagcg gcctgctgaa ggagagtatg cgcatcaaga tgtacatgga gggcaccgtg | 60 |
| aacggccact acttcaagtg cgagggcgag ggcgacggca ccccttcgc cggcacccag | 120 |
| agcatgagaa tccacgtgac cgagggcgcc cccctgccct tcgccttcga tatcctggcc | 180 |
| ccctgctgcg agtacggcag caggaccttc gtgcaccaca ccgccgagat ccccgacttc | 240 |
| ttcaagcaga gcttccccga gggcttcacc tgggagagaa ccaccaccta cgaggacggc | 300 |
| ggcatcctga ccgccaccca ggacaccagc ctggagggca ctgcctgat ctacaaggtg | 360 |
| aaggtgcacg gcaccaactt ccccgccgac ggccccgtga tgaagaacaa gagcggcggc | 420 |

```
tgggagccca gcaccgaggt ggtgtacccc gagaacggcg tgctgtgcgg ccggaacgtg    480
atggccctga aggtgggcga ccggcacctg atctgccacc actacaccag ctaccggagc    540
aagaaggccg tgcgcgccct gaccatgccc ggcttccact tcaccgacat ccggctccag    600
atgctgcgga agaagaagga cgagtacttc gagctgtacg aggccagcgt ggcccggtac    660
agcgacctgc ccgagaaggc caactga                                        687
```

<210> SEQ ID NO 135
<211> LENGTH: 687
<212> TYPE: DNA
<213> ORGANISM: Artificial sequence
<220> FEATURE:
<223> OTHER INFORMATION: HcRed1 ORF modified Reef Coral - human codon optimized

<400> SEQUENCE: 135

```
atggtcagcg gcctcctcaa agagtccatg cgcattaaaa tgtacatgga gggcaccgtc     60
aacggccact acttcaagtg cgagggcgag ggcgacggca cccccttcgc cggcacccag    120
tctatgcgga tccacgtcac cgagggcgcc cccctcccct tcgccttcga catcctcgcc    180
ccttgttgcg agtacggcag cagaaccttc gtccaccaca ccgccgagat ccccgacttc    240
ttcaaacaga gcttccccga gggcttcact tgggagagaa ccaccaccta cgaggacggc    300
ggcatcctca ccgcccacca ggacaccagc ctcgagggca ctgcctcat ctacaaggtc    360 aaagtccacg gcaccaactt ccccgccgac ggccccgtca tgaaaaacaa agcggcggt    420 tgggagccca gcaccgaggt cgtctacccc gagaacggcg tcctttgcgg ccggaacgtc    480
atggccctca agtcggcga ccggcacctc atttgccacc actacaccag ctaccggagc    540
aaaaaagccg tccgcgccct caccatgccc ggcttccact tcaccgacat ccggctccag    600
atgctccgga aaaaaaaga cgagtacttc gagctctacg aggccagcgt ggcccggtac    660
agcgacctcc ccgagaaagc caattga                                        687
```

<210> SEQ ID NO 136
<211> LENGTH: 687
<212> TYPE: DNA
<213> ORGANISM: artificial sequence
<220> FEATURE:
<223> OTHER INFORMATION: HcRed1 ORF partially modified Reef Coral - human codon optimized

<400> SEQUENCE: 136

```
atggtcagcg gcctcctcaa agagtccatg cgcattaaaa tgtacatgga gggcaccgtc     60
aacggccact acttcaagtg cgagggcgag ggcgacggca cccccttcgc cggcacccag    120
agcatgagaa tccacgtgac cgagggcgcc cccctgccct tcgccttcga catcctggcc    180
ccctgctgcg agtacggcag caggaccttc gtgcaccaca ccgccgagat ccccgacttc    240
ttcaagcaga gcttccccga gggcttcacc tgggagagaa ccaccaccta cgaggacggc    300
ggcatcctga ccgcccacca ggacaccagc ctggagggca ctgcctgat ctacaaggtg    360 aaggtgcacg gcaccaactt ccccgccgac ggccccgtga tgaagaacaa gagcggcggc    420
tgggagccca gcaccgaggt ggtgtacccc gagaacggcg tgctgtgcgg ccggaacgtg    480
atggccctga aggtgggcga ccggcacctg atctgccacc actacaccag ctaccggagc    540
aagaaggccg tgcgcgccct gaccatgccc ggcttccact tcaccgacat ccggctccag    600
atgctgcgga agaagaagga cgagtacttc gagctgtacg aggccagcgt ggcccggtac    660
```

```
<210> SEQ ID NO 137
<211> LENGTH: 744
<212> TYPE: DNA
<213> ORGANISM: human
<220> FEATURE:
<223> OTHER INFORMATION: Mutated Anti-Thy VL ORF with CD5 signal
      peptide

<400> SEQUENCE: 137
atgcccatgg ggtctctgca accgctggcc accttgtacc tgctggggat gctggtcgct    60
tccgtgctag cggatatcct cgtgatgacc cagtctccag tcaccctgtc tttgtcttca   120
ggggaaagag ccaccctctc ctgcagggcc agtcagagta ttagtaactc cttagcctgg   180
taccaacaga aacctggcct ggctcccagg ctcctcatct atgatgcatc aacagggcc    240
actggcgtcc cagccaggtt cagtggcagt gggtctggga cagacttcaa tctcaccatc   300
agcagcttca atctcaccat cagcagccta gaccctgaag atgttgcagt gtattactgt   360
caccagcgta gcaactggcc tcctttcact ttcggcggag ggaccaaggt ggagatcaaa   420
cgtacggtgg ctgcaccatc tgtcttcatc ttcccgccat ctgatgagca gttgaaatct   480
ggaactgcct ctgttgtgtg cctgctgaat aacttctatc ccagagaggc caaagtacag   540
tggaaggtgg ataacgccct ccaatcgggt aactcccagg agagtgtcac agagcaggac   600
agcaaggaca gcacctacag cctcagcagc accctgacgc tgagcaaagc agactacgag   660
aaacacaaag tctacgcctg cgaagtcacc catcagggcc tgagctcgcc cgtcacaaag   720
agcttcaaca ggggagagtg ttag                                         744

<210> SEQ ID NO 138
<211> LENGTH: 744
<212> TYPE: DNA
<213> ORGANISM: human
<220> FEATURE:
<223> OTHER INFORMATION: Mutated Anti-Thy VL ORF with CD5 signal peptide

<400> SEQUENCE: 138
atgcccatcg ggtctctgca accgctggcc accttgtacc tgctggggat cctggtcgct    60
tccgtgctag cggatatcct cgtgatgacc cagtctccag tcaccctgtc tttgtcttca   120
ggggaaagag ccaccctctc ctgcagggcc agtcagagta ttagtaactc cttagcctgg   180
taccaacaga aacctggcct ggctcccagg ctcctcatct atgatgcatc aacagggcc    240
actggcgtcc cagccaggtt cagtggcagt gggtctggga cagacttcaa tctcaccatc   300
agcagcttca atctcaccat cagcagccta gaccctgaag atgttgcagt gtattactgt   360
caccagcgta gcaactggcc tcctttcact ttcggcggag ggaccaaggt ggagatcaaa   420
cgtacggtgg ctgcaccatc tgtcttcatc ttcccgccat ctgatgagca gttgaaatct   480
ggaactgcct ctgttgtgtg cctgctgaat aacttctatc ccagagaggc caaagtacag   540
tggaaggtgg ataacgccct ccaatcgggt aactcccagg agagtgtcac agagcaggac   600
agcaaggaca gcacctacag cctcagcagc accctgacgc tgagcaaagc agactacgag   660
aaacacaaag tctacgcctg cgaagtcacc catcagggcc tgagctcgcc cgtcacaaag   720
agcttcaaca ggggagagtg ttag                                         744

<210> SEQ ID NO 139
<211> LENGTH: 744
<212> TYPE: DNA
```

<213> ORGANISM: human
<220> FEATURE:
<223> OTHER INFORMATION: Mutated Anti-Thy VL ORF with CD5 signal peptide

<400> SEQUENCE: 139

```
atgcccatgg ggtctctcca accgctcgcc accttgtacc tcctcgggat gctcgtcgct      60
tccgtgctag cggatatcct cgtgatgacc cagtctccag tcaccctgtc tttgtcttca     120
ggggaaagag ccaccctctc ctgcagggcc agtcagagta ttagtaactc cttagcctgg     180
taccaacaga aacctggcct ggctcccagg ctcctcatct atgatgcatc caacagggcc     240
actggcgtcc cagccaggtt cagtggcagt gggtctggga cagacttcaa tctcaccatc     300
agcagcttca atctcaccat cagcagccta gaccctgaag atgttgcagt gtattactgt     360
caccagcgta gcaactggcc tcctttcact ttcggcggag ggaccaaggt ggagatcaaa     420
cgtacggtgg ctgcaccatc tgtcttcatc ttcccgccat ctgatgagca gttgaaatct     480
ggaactgcct ctgttgtgtg cctgctgaat aacttctatc ccagagaggc caaagtacag     540
tggaaggtgg ataacgccct ccaatcgggt aactcccagg agagtgtcac agagcaggac     600
agcaaggaca gcacctacag cctcagcagc accctgacgc tgagcaaagc agactacgag     660
aaacacaaag tctacgcctg cgaagtcacc catcagggcc tgagctcgcc cgtcacaaag     720
agcttcaaca ggggagagtg ttag                                            744
```

<210> SEQ ID NO 140
<211> LENGTH: 744
<212> TYPE: DNA
<213> ORGANISM: human
<220> FEATURE:
<223> OTHER INFORMATION: Mutated Anti-Thy VL ORF with CD5 signal peptide

<400> SEQUENCE: 140

```
atgcccatcg ggtctctcca accgctcgcc accttgtacc tcctcgggat cctcgtcgct      60
tccgtgctag cggatatcct cgtgatgacc cagtctccag tcaccctgtc tttgtcttca     120
ggggaaagag ccaccctctc ctgcagggcc agtcagagta ttagtaactc cttagcctgg     180
taccaacaga aacctggcct ggctcccagg ctcctcatct atgatgcatc caacagggcc     240
actggcgtcc cagccaggtt cagtggcagt gggtctggga cagacttcaa tctcaccatc     300
agcagcttca atctcaccat cagcagccta gaccctgaag atgttgcagt gtattactgt     360
caccagcgta gcaactggcc tcctttcact ttcggcggag ggaccaaggt ggagatcaaa     420
cgtacggtgg ctgcaccatc tgtcttcatc ttcccgccat ctgatgagca gttgaaatct     480
ggaactgcct ctgttgtgtg cctgctgaat aacttctatc ccagagaggc caaagtacag     540
tggaaggtgg ataacgccct ccaatcgggt aactcccagg agagtgtcac agagcaggac     600
agcaaggaca gcacctacag cctcagcagc accctgacgc tgagcaaagc agactacgag     660
aaacacaaag tctacgcctg cgaagtcacc catcagggcc tgagctcgcc cgtcacaaag     720
agcttcaaca ggggagagtg ttag                                            744
```

<210> SEQ ID NO 141
<211> LENGTH: 744
<212> TYPE: DNA
<213> ORGANISM: human
<220> FEATURE:
<223> OTHER INFORMATION: Mutated Anti-Thy VL ORF with CD5 signal peptide

<400> SEQUENCE: 141

```
atggctatcg ggtctctcca accgctcgcc accttgtacc tcctcgggat cctcgtcgct      60
```

-continued

| | |
|---|---|
| tccgtgctag cggatatcct cgtgatgacc cagtctccag tcaccctgtc tttgtcttca | 120 |
| ggggaaagag ccaccctctc ctgcagggcc agtcagagta ttagtaactc cttagcctgg | 180 |
| taccaacaga aacctggcct ggctcccagg ctcctcatct atgatgcatc caacagggcc | 240 |
| actggcgtcc cagccaggtt cagtggcagt gggtctggga cagacttcaa tctcaccatc | 300 |
| agcagcttca atctcaccat cagcagccta gaccctgaag atgttgcagt gtattactgt | 360 |
| caccagcgta gcaactggcc tcctttcact ttcggcggag ggaccaaggt ggagatcaaa | 420 |
| cgtacggtgg ctgcaccatc tgtcttcatc ttcccgccat ctgatgagca gttgaaatct | 480 |
| ggaactgcct ctgttgtgtg cctgctgaat aacttctatc ccagagaggc caaagtacag | 540 |
| tggaaggtgg ataacgccct ccaatcgggt aactcccagg agagtgtcac agagcaggac | 600 |
| agcaaggaca gcacctacag cctcagcagc accctgacgc tgagcaaagc agactacgag | 660 |
| aaacacaaag tctacgcctg cgaagtcacc catcagggcc tgagctcgcc cgtcacaaag | 720 |
| agcttcaaca ggggagagtg ttag | 744 |

<210> SEQ ID NO 142
<211> LENGTH: 24
<212> TYPE: RNA
<213> ORGANISM: human
<220> FEATURE:
<223> OTHER INFORMATION: Mutated miR-183 binding sequence

<400> SEQUENCE: 142

| | |
|---|---|
| aaagcggaua cucacuggac acca | 24 |

<210> SEQ ID NO 143
<211> LENGTH: 756
<212> TYPE: DNA
<213> ORGANISM: Artificial sequence
<220> FEATURE:
<223> OTHER INFORMATION: miR-183 CAT FLAG sequence

<400> SEQUENCE: 143

| | |
|---|---|
| atggagaaaa aaatcacagg atataccacc gttgatatat cccaatggca tcgtaaagaa | 60 |
| cattttcagg catttcagtc agttgctcaa tgtacctata accagaccgt tcagctggat | 120 |
| attacggcct ttttaaagac cgtaaagaaa aataagcaca gttttatcc ggcctttatt | 180 |
| cacattcttg cccgcctgat gaatgctcat ccggaaaagc gaattctcac aggccatcat | 240 |
| ccggaactcc gtatggcaat gaaagacggt gagctggtga tatgggatag tgttcaccct | 300 |
| tgttacaccg ttttccatga gcaaactgaa acgttttcat cgctctggag tgaataccac | 360 |
| gacgatttcc ggcagtttct acacatatat tcgcaagatg tggcgtgtta cggtgaaaac | 420 |
| ctggcctatt tccctaaagg gtttattgag aatatgtttt tcgtctcagc caatccctgg | 480 |
| gtgagtttca ccagttttga tttaaacgtg gccaatatgg acaacttctt cgcccccgtt | 540 |
| ttcacgatgg gcaaatatta tacgcaaggc gacaaggtgc tgatgccgct ggcgattcag | 600 |
| gttcatcatg ccgtttgtga tggcttccat gtcggcagaa tgcttaatga attacaacag | 660 |
| tactgcgatg agtggcaggg cggggcggac tacaaagacc atgacggtga ttataaagat | 720 |
| catgacatcg attacaagga tgacgatgac aagtaa | 756 |

<210> SEQ ID NO 144
<211> LENGTH: 756
<212> TYPE: DNA
<213> ORGANISM: Artificial sequence
<220> FEATURE:

<223> OTHER INFORMATION: Mutated miR-183 CAT FLAG sequence

<400> SEQUENCE: 144

| | |
|---|---|
| atggagaaaa aaatcacagg atataccacc gttgatatat cccaatggca tcgtaaagaa | 60 |
| cattttcagg catttcagtc agttgctcaa tgtacctata accagaccgt tcagctggat | 120 |
| attacggcct ttttaaagac cgtaaagaaa ataagcaca agttttatcc ggcctttatt | 180 |
| cacattcttg cccgcctgat gaatgctcat ccggaaaagc ggatactcac tggacaccat | 240 |
| ccggaactcc gtatggcaat gaaagacggt gagctggtga tatgggatag tgttcaccct | 300 |
| tgttacaccg ttttccatga gcaaactgaa acgttttcat cgctctggag tgaataccac | 360 |
| gacgatttcc ggcagtttct acacatatat tcgcaagatg tggcgtgtta cggtgaaaac | 420 |
| ctggcctatt tccctaaagg gtttattgag aatatgtttt tcgtctcagc caatccctgg | 480 |
| gtgagtttca ccagttttga tttaaacgtg gccaatatgg acaacttctt cgcccccgtt | 540 |
| ttcacgatgg gcaaatatta tacgcaaggc gacaaggtgc tgatgccgct ggcgattcag | 600 |
| gttcatcatg ccgtttgtga tggcttccat gtcggcagaa tgcttaatga attacaacag | 660 |
| tactgcgatg agtggcaggg cggggcggac tacaaagacc atgacggtga ttataaagat | 720 |
| catgacatcg attacaagga tgacgatgac aagtaa | 756 |

<210> SEQ ID NO 145
<211> LENGTH: 93
<212> TYPE: DNA
<213> ORGANISM: Pichia pastoris
<220> FEATURE:
<223> OTHER INFORMATION: Kar2 signal peptide

<400> SEQUENCE: 145

| | |
|---|---|
| atgctgtcgt taaaccatc ttggctgact ttggcggcat taatgtatgc catgctattg | 60 |
| gtcgtagtgc catttgctaa acctgttaga gct | 93 |

<210> SEQ ID NO 146
<211> LENGTH: 93
<212> TYPE: DNA
<213> ORGANISM: pichia pastoris
<220> FEATURE:
<223> OTHER INFORMATION: Rescue version of signal peptide

<400> SEQUENCE: 146

| | |
|---|---|
| atgctctcgt taaaccatc ttggctcact ttggcggcat taatttacgc catcctattg | 60 |
| gtcgtagtgc catttgctaa acccgttaga gct | 93 |

<210> SEQ ID NO 147
<211> LENGTH: 78
<212> TYPE: DNA
<213> ORGANISM: Gallus gallus
<220> FEATURE:
<223> OTHER INFORMATION: Lysozyme signal sequence

<400> SEQUENCE: 147

| | |
|---|---|
| atgctgggta agaaggaccc aatgtgtctt gttttggtct tgttgggatt gactgctttg | 60 |
| ttgggtatct gtcaaggt | 78 |

<210> SEQ ID NO 148
<211> LENGTH: 78
<212> TYPE: DNA
<213> ORGANISM: Gallus gallus
<220> FEATURE:
<223> OTHER INFORMATION: Rescue version signal sequence

```
<400> SEQUENCE: 148
atgctcggta agaacgaccc aatttgtctt gttttggtct tgttgggatt gaccgctttg    60
ttgggtattt gtcaaggt                                                  78

<210> SEQ ID NO 149
<211> LENGTH: 69
<212> TYPE: DNA
<213> ORGANISM: human
<220> FEATURE:
<223> OTHER INFORMATION: granulocyte colony-stimulating factor receptor
      precursor

<400> SEQUENCE: 149
atgaggctgg gaaactgcag cctgacttgg gctgccctga tcatcctgct gctccccgga    60
agtctggag                                                            69

<210> SEQ ID NO 150
<211> LENGTH: 69
<212> TYPE: DNA
<213> ORGANISM: human
<220> FEATURE:
<223> OTHER INFORMATION: Rescue version signal sequence

<400> SEQUENCE: 150
atgaggcttg gaaattgtag cctcacttgg gccgccctca tcatcctcct tctccccgga    60
agtctcgag                                                            69

<210> SEQ ID NO 151
<211> LENGTH: 70
<212> TYPE: DNA
<213> ORGANISM: human
<220> FEATURE:
<223> OTHER INFORMATION: calcitonin receptor precursor signal sequence

<400> SEQUENCE: 151
atgaggacat ttacaagccg gtgcttggca ctgtttcttc ttctaaatca cccaacccca    60
attcttcctg                                                           70

<210> SEQ ID NO 152
<211> LENGTH: 70
<212> TYPE: DNA
<213> ORGANISM: human
<220> FEATURE:
<223> OTHER INFORMATION: Rescue version signal sequence

<400> SEQUENCE: 152
atgaggacat ttacaagccg ttgcttggca ctctttcttc ttctaaatca cccaacccca    60
attcttcccg                                                           70

<210> SEQ ID NO 153
<211> LENGTH: 69
<212> TYPE: DNA
<213> ORGANISM: human
<220> FEATURE:
<223> OTHER INFORMATION: Cell adhesion molecule 3 precursor

<400> SEQUENCE: 153
atggccccag ccgcctcgct cctgctcctg ctcctgctgt tcgcctgctg ctgggcgccc    60
ggcggggcc                                                            69
```

```
<210> SEQ ID NO 154
<211> LENGTH: 69
<212> TYPE: DNA
<213> ORGANISM: human
<220> FEATURE:
<223> OTHER INFORMATION: Rescue version signal sequence

<400> SEQUENCE: 154
atggccccag ccgcctcgct ccttctcctt ctccttctct ttgcttgttg ttgggcgccc    60
ggcggggcc                                                           69

<210> SEQ ID NO 155
<211> LENGTH: 66
<212> TYPE: DNA
<213> ORGANISM: human
<220> FEATURE:
<223> OTHER INFORMATION: HLA class I histocompatibility antigen signal
      sequence

<400> SEQUENCE: 155
atggtcgcgc cccgaaccct cctcctgcta ctctcggggg ccctggccct gacccagacc    60
tgggcg                                                              66

<210> SEQ ID NO 156
<211> LENGTH: 66
<212> TYPE: DNA
<213> ORGANISM: human
<220> FEATURE:
<223> OTHER INFORMATION: Rescue version signal sequence

<400> SEQUENCE: 156
atggtcgcgc cccgaaccgt cctccttctt ctctcggcgg ccctcgccct taccgagact    60
tgggcc                                                              66
```